US00RE49834E

(19) United States
(12) Reissued Patent
Liang

(10) Patent Number: US RE49,834 E
(45) **Date of Reissued Patent: *Feb. 13, 2024**

(54) JAK1 SELECTIVE INHIBITORS AND USES THEREOF

(71) Applicant: Hangzhou Highlightll Pharmaceutical Co., LTD, Hangzhou (CN)

(72) Inventor: Congxin Liang, Palm Beach Gardens, FL (US)

(73) Assignee: Hangzhou Highlightll Pharmaceutical Co., Ltd., Iselin, NJ (US)

( * ) Notice: This patent is subject to a terminal disclaimer.

(21) Appl. No.: 17/526,799

(22) Filed: Nov. 15, 2021

Related U.S. Patent Documents

Reissue of:
(64) Patent No.: 10,738,060
Issued: Aug. 11, 2020
Appl. No.: 16/333,994
PCT Filed: Sep. 30, 2017
PCT No.: PCT/US2017/054668
§ 371 (c)(1),
(2) Date: Mar. 15, 2019
PCT Pub. No.: WO2018/067422
PCT Pub. Date: Apr. 12, 2018

U.S. Applications:
(60) Provisional application No. 62/403,660, filed on Oct. 3, 2016.

(51) Int. Cl.
*C07D 491/147* (2006.01)
*A61P 19/02* (2006.01)
*C07D 211/00* (2006.01)

(52) U.S. Cl.
CPC ..... *C07D 491/147* (2013.01); *A61P 19/02* (2018.01); *C07D 211/00* (2013.01)

(58) Field of Classification Search
CPC ..... C07D 491/147; C07D 211/00; C07D 491/048; A61P 19/02; A61P 29/00; A61P 35/00; A61P 37/06; A61P 37/00; A61K 31/4155; A61K 31/437; A61K 31/519
See application file for complete search history.

(56) References Cited

U.S. PATENT DOCUMENTS

| | | | |
|---|---|---|---|
| 10,738,060 | B2 | 8/2020 | Liang |
| 2007/0185152 | A1 | 8/2007 | Yamashita et al. |
| 2012/0122846 | A1 | 5/2012 | Caldenwood et al. |
| 2015/0342952 | A1 | 12/2015 | Leopold et al. |
| 2015/0344497 | A1 | 12/2015 | Zhou et al. |

FOREIGN PATENT DOCUMENTS

| | | | |
|---|---|---|---|
| EP | 1 104 764 | A1 | 6/2001 |
| EP | 1104764 | | 6/2001 |
| WO | WO 2013/024895 | | 2/2013 |
| WO | WO 2013/024895 | A1 | 2/2013 |
| WO | WO 2014/071031 | | 5/2014 |
| WO | WO 2014/071031 | A1 | 5/2014 |
| WO | WO 2015/168246 | A1 | 11/2015 |

OTHER PUBLICATIONS

International Search Report and Written Opinion for PCT/US2017/054668 dated Dec. 15, 2017. 8 pages.
Extended European Search Report for EP App. No. 17858944.6 dated Feb. 25, 2020. 9 pages.
[No Author Listed] Bioisosteres. In: Medicinal Chemistry, Second Edition. 2003. You et al., Eds. Section 3, Chapter 24:583-5.
Silverman, The Organic Chemistry of Drug Design and Drug Action, Second Edition. 2004:29-34.

*Primary Examiner* — Alan D Diamond
(74) *Attorney, Agent, or Firm* — Wolf, Greenfield & Sacks, P.C.

(57) ABSTRACT

The new 1H-furo[3,2-b]imidazo[4,5-d]pyridine derivatives are selective Jak1 kinase inhibitors useful in treating disorders related to Jak1 activities such as autoimmune diseases or disorders, inflammatory diseases or disorders, and cancer or neoplastic diseases or disorders.

22 Claims, No Drawings

JAK1 SELECTIVE INHIBITORS AND USES THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

*Notice: More than one reissue application has been filed for the reissue of U.S. Pat. No. 10,738,060. The reissue applications are application Ser. Nos. 17/526,799, 18/122,295, and 18/386,142, all of which are reissues of U.S. Pat. No. 10,738,060.*

The present application *is a reissue application of U.S. Pat. No. 10,738,060, issued Aug. 11, 2020, filed as U.S. patent application Ser. No. 16/333,994 on Mar. 15, 2019, which* is a national stage application of International Application PCT/US2017/054668, filed Sep. 30, 2017, which claims the benefit under 35 U.S.C. § 119(e) of U.S. Provisional Application [Ser.] No. 62/403,660, filed Oct. 3, 2016, the contents of each of which are incorporated *herein* by reference in their entireties into the present disclosure.

TECHNICAL FIELD OF THE INVENTION

This invention relates to novel 1H-furo[3,2-b]imidazo[4,5-d]pyridine derivatives, their pharmaceutically acceptable salts, solvates, hydrates and polymorphs thereof as selective Jak1 kinase inhibitors. The invention also provides compositions comprising a compound of this invention and the use of such compositions in methods of treating diseases and conditions associated with Jak1 and are useful in treating disorders related to Jak1 activities such as an autoimmune disease or disorder, an inflammatory disease or disorder, and a cancer or neoplastic disease or disorder.

BACKGROUND OF THE INVENTION

The protein kinases represent a large family of proteins that play a central role in the regulation of a wide variety of cellular processes and maintenance of cellular function. A partial, non-limiting, list of these kinases include: non-receptor tyrosine kinases such as the Janus kinase family (Jak1, Jak2, Jak3 and Tyk2); receptor tyrosine kinases such as platelet-derived growth factor receptor kinase (PDGFR); and serine/threonine kinases such as b-RAF. Aberrant kinase activity has been observed in many disease states including benign and malignant proliferative disorders as well as diseases resulting from inappropriate activation of the immune and nervous systems. The compounds of this invention selectively inhibit the activity of one or more protein kinases over other related kinases, and are thus expected to be useful in the treatment of diseases mediated by the selectively inhibited kinase(s) while avoiding the undesirable side effects associated with the inhibition of the related kinase(s).

In particular, the Janus kinase family comprises 4 known family members: Jak 1, 2, 3, and tyrosine kinase 2 (Tyk2). These cytoplasmic tyrosine kinases are associated with membrane cytokine receptors such as common gamma-chain receptors and the glycoprotein 130 (gp 130) trans-membrane proteins (Murray, J. Immunol. 178(5):2623-2629, 2007). Almost 40 cytokine receptors signal through combinations of these 4 Jak family members and their 7 downstream substrates: the signal transduction activators of transcription (STAT) family members (Ghoreschi et al., Immunol Rev. 228(1):273-287, 2009). Cytokine binding to its receptor initiates Jak activation via trans- and auto-phosphorylation. The Jak family kinases in turn phosphorylate cytokine receptor residues, creating binding sites for sarcoma homology 2 (SH2) containing proteins, such as the STAT factors and other regulators, which are subsequently activated by Jak phosphorylation. Activated STATs enter the nucleus initiating expression of survival factors, cytokines, chemokines, and molecules that facilitate leukocyte cellular trafficking (Schindler et al., J. Biol. Chem. 282(28):20059-20063, 2007). Jak activation also results in cell proliferation via phosphoinositide 3-kinase (PI3K) and protein kinase B-mediated pathways.

Jak3 and Jak1 are components of the common gamma-chain cytokine receptor complexes, and blockade of either inhibits signaling by inflammatory cytokines: interleukin (IL)-2, 4, 7, 9, 15, and 21 (Ghoreschi et al., Immunol. Rev. 228(1):273-287, 2009). By contrast, other pathologically relevant cytokines, such as IL-6, depend uniquely on Jak1. Hence, Jak1 blockade inhibits signaling of many pro-inflammatory cytokines (Guschin et al., EMBO J. 14(7):1421-1429, 1995). Clinical efficacy in rheumatoid arthritis (RA) has been observed with the IL-6 receptor neutralizing antibody, tocilizumab (Maini et al., Arthritis Rheum. 54(9):2817-2829, 2006).

Humans deficient in Jak1 and Jak2 have not been described. Mice lacking Jak1 die perinatally (Schindler et al., J. Biol Chem. 282(28):20059-20063, 2007). Jak2 deficiency in mice is also lethal, with $Jak2^{-/-}$ embryos dying between Day 12 and Day 13 after conception because of deficits in erythropoiesis (Neubauer et al., Cell 93(3):397-409, 1998). Jak3 deficiency has been described in humans and presents as severe combined immunodeficiency in the first few months of life, with symptoms such as failure to thrive, severe and recurrent infections, thrush, and diarrhea. Infants with Jak3 deficiency have an absence of circulating T cells and NK cells and abnormal B cell function. Tyk2-deficiency additionally has been described in humans, manifesting with impaired antimicrobial responses, elevated serum IgE, and atopic dermatitis (Minegishi et al., Immunity 25(5):745-755, 2006).

Given the high degree of structural similarity between Jak1 and Jak2 (Williams et al., J. Mal. Biol. 387(1):219-232, 2009), the literature suggests that the majority of Jak1 inhibitors also inhibit Jak2 (Incyte Corp. press release, 10 Nov. 2010; Changelian et al., Science 302(5646):875-878, 2003).

Anti-cytokine therapies have become standard in the treatment of RA. In humans, a growing body of evidence suggests that Jak1 inhibition is an effective therapy for the treatment of signs and symptoms of RA. Multiple clinical trials administering Pfizer's Jak 1/3 inhibitor tofacitinib (Kremer et al., Arthritis Rheum. 60(7):1895-1905, 2009; Riese et al. Best Pract. Res. Clin. Rheumatol. 24(4):513-526, 2010), Incyte/Lilly's Jak1/2 inhibitor INCB-28050/LY3009104 (Incyte Corp. press release, 10 Nov. 2010), or Galapagos' Jak1 inhibitor GLP0634 (Galapagos Nev. press release, 22 Nov. 2011) have demonstrated statistically significant efficacy in this disease.

Tofacitinib, an inhibitor of Jak1, and Jak3, has been approved in the United States and additional countries around the world for the indication of adult patients with moderately to severely active RA who have had an inadequate response or intolerance to methotrexate (MTX), used as monotherapy or in combination with MTX or other non-biologic DMARDs. Safety data from Phase 2 and Phase 3 studies in patients (Fleischmann, Curr. Opin. Rheumatol. 24(3):335-341, 2012; Kremer et al., Arthritis Rheum. 64(4): 970-981, 2012; Fleischmann et al., Arthritis Rheum. 64(3): 617-629, 2012) with RA for tofacitinib compared with placebo have indicated that the most common serious adverse reactions are infections, including pneumonia, cellulitis, herpes zoster, and urinary tract infection. In addition, tuberculosis (including cases of disseminated tuberculosis) and opportunistic infections such as other mycobacterial infections, cryptococcus, esophageal candidiasis, pneumocystosis, multidermatomal herpes zoster, cytomegalovirus, and BK virus were reported. Lymphoma and other malignancies have been observed in patients treated with tofacitinib. Epstein-Barr virus-associated post-transplant lymphoproliferative disorder has been observed at an increased rate in renal transplant patients treated with tofacitinib and concomitant immunosuppressive medications. Gastrointestinal perforations in patients receiving tofacitinib also were reported. In addition, laboratory abnormalities have been described, including dose-related decreases in absolute neutrophil counts as well as hemoglobin. Furthermore, small increases in liver transaminases (alanine aminotransferase [ALT], aspartate aminotransferase [AST]) and serum creatinine, and elevated LDL, HDL, and total cholesterol levels have been reported.

A Phase 2 study of VX-509 (inhibitor of Jak3) in patients with RA also has shown an increased risk of infections and increases in lipid levels (Fleischmann et al., Arthritis Rheum. 63:LB3, 2011).

A 52-week, open-label, long-term extension Phase 2b study of baricitinib—an orally administered selective Jak1 and Jak2 inhibitor—in 201 patients with active RA found no opportunistic infections, cases of tuberculosis, or lymphomas. Clinically significant laboratory abnormalities were infrequently observed (increased ALT, anemia, increased creatine kinase [CK], pancytopenia, reported in one subject each); one subject discontinued due to a laboratory abnormality (increased ALT). One death occurred and was attributed to presumed myocardial infarction (Keystone et al., Ann. Rheum. Dis. 71(Suppl 3):152, 2012; Genovese et al., Arthritis Rheum. 64 (Suppl 10):2487, 2012; Taylor et al., abstract OP0047, EULAR 2013, the Annual Congress of the European League Against Rheumatism. 2013 Jun. 12-15; Madrid, Spain).

Despite the seemingly numerous treatment options, however, many RA patients fail to experience substantial decreases in disease activity. Although earlier studies have shown that Jak blockade may be effective in managing disease and achieving remission, the first generation Jak inhibitors (such as tofacitinib and baricitinib) have failed to reach their full potential, at least partly due to their tolerability and safety issues that limit dose.

Specifically, the first generation Jak inhibitors tofacitinib and baricitinib have been characterized as Jak1/Jak3 and Jak1/Jak2 inhibitors, respectively (Fridman et al., J. Immunol., 184:5298-5307, 2010; Meyer et al., J. Inflamm. (Lond.) 7:41, 2010; and Taylor et al., Rheumatology 52:i44-i55, 2013). Despite the initial encouraging results, these first generation Jak inhibitors have failed to reach their full potential due to tolerability issues that limited dose (Fleischmann et al., Curr. Opin. Rheumatol. 24:335-341, 2012; Riese et al., Best Pract. Res. Clin. Rheumatol. 24:513-526, 2010). JAKs are known to play roles in the regulation of over forty pathways (Murray, J. Immunol. 178:2623-2629, 2007). However, despite the high selectivity of these two compounds for JAKs over other kinase families, these inhibitors may not be optimally selective for kinases within the JAK family. For instance, incidence of severe anemia was reported to be a dose limiting factor during Tofacitinib Phase II development in RA (Pfizer, Investigators Brochure. In FDA Advisory Board (Bethesda Md.), 2012; Riese et al., Best Pract. Res. Clin. Rheumatol. 24:513-526, 2010). Moreover, increases in herpes virus infections, potentially secondary to decreases in NK cell counts, were reported in Phase III tofacitinib trials (O'Shea et al., Ann. Rheum. Dis. 72(Suppl 2):ii 111-115, 2013; Pfizer, Investigators Brochure. In FDA Advisory Board (Bethesda Md.), 2012). It is reasonable that these effects could arise due to inhibition of EPO and IL-15 signaling via Jak2 and Jak3 respectively (Jost and Altfeld, Annu. Rev. Immunol. 31:163-194, 2013; Kennedy et al., J. Exp. Med. 191:771-780, 2000; and Richmond et al., Trends Cell Biol. 15:146-155, 2005). Indeed, failure of interventions to treat anemia associated with RA may limit chances for a fully successful response to treatment.

Thus, there is a medical need unmet by the current treatment options using Jak inhibitors. Efforts to identify Jak1 selective inhibitors are on-going (Zak et al. J. Med. Chem. 2013, 56, 4764-4785; Menet et al. Future Med. Chem. 2015, 7, 203-235; WO2013/007768). Prominent Jak1 selective compounds in development are GLP0634, ABT-494 (WO2015/061665), and the compound in a recent patent publication from Incyte (WO2015/168246), but no Jak1 selective inhibitor has been approved yet.

Herein, novel 1H-furo[3,2-b]imidazo[4,5-d]pyridine derivatives are described as Jak1 selective inhibitors. These compounds, and compositions comprising a compound of this invention are useful in treating disorders related to Jak1 activities such as an autoimmune disease or disorder, or an inflammatory disease or disorder, and a cancer or neoplastic disease or disorder.

SUMMARY OF THE INVENTION

This invention discloses novel 1H-furo[3,2-b]imidazo[4,5-d]pyridine derivatives their pharmaceutically acceptable salts, solvates, hydrates and polymorphs thereof as selective Jak1 kinase inhibitors. The invention also provides compositions comprising a compound of this invention and the use of such compositions in methods of treating diseases and conditions associated with Jak1.

The present invention solves the problems set forth above by providing an isolated compound of Formula I:

I

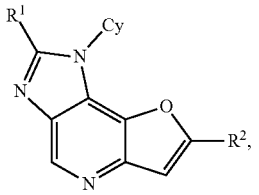

or a pharmaceutically acceptable salt thereof; or a prodrug, or a pharmaceutically acceptable salt of a prodrug thereof; or a hydrate, solvate, or polymorph thereof; wherein:

$R^1$ is H, halo, or $C_{1-3}$ alkyl optionally substituted with 1, 2, or 3 substituents independently selected from the group consisting of halo, OH, CN, OR, NHR, NRR', N(R)C(=O)R', N(R)C(=O)(O)R', OC(=O)NRR', C(=O)R, C(=O)NRR', N(R)S(O)$_2$R', S(O)$_2$R, and S(O)$_2$NRR$^1$;

R$^2$ is H, halo, or C$_{1-3}$ alkyl;

Cy is C$_{3-7}$ cycloalkyl, 3-7 membered heterocyclyl, phenyl, or 5-6 membered heteroaryl, each optionally substituted with 1, 2, or 3 substituents independently selected from the group consisting of R$^3$, oxo, halo, OH, CN, OR, NHR, NRR', N(R)C(=O)R', N(R)C(=O)(O)R', OC(=O)NRR', C(=O)R, C(=O)NRR', N(R)S(O)$_2$R', S(O)$_2$R, and S(O)$_2$NRR', wherein R$^3$ is C$_{1-3}$ alkyl optionally substituted with 1, 2, or 3 substituents independently selected from the group consisting of halo, OH, CN, OR, NHR, NRR', N(R)C(=O)R', N(R)C(=O)(O)R', OC(=O)NRR', C(=O)R, C(=O)NRR', N(R)S(O)$_2$R', S(O)$_2$R, and S(O)$_2$NRR';

R, R' each is independently H, or C$_{1-3}$ alkyl optionally substituted with 1, 2, or 3 substituents independently selected from the group consisting of halo, OH, and CN.

The compounds of this invention, and compositions comprising them, are useful for treating or lessening the severity of Jak1 modulated diseases, disorders, or symptoms thereof.

In another aspect, the invention relates to a method of treating a disease or disease symptom in a subject in need thereof including administering to the subject an effective amount of a compound of formula I herein, or pharmaceutically acceptable salt, solvate or hydrate thereof (or composition thereof). The disease or disease symptom can be any of those modulated by Jak1. The disease or disease symptom can be, for example, an autoimmune disease or disorder such as rheumatoid arthritis or an inflammatory disease or disorder, and cancer or neoplastic proliferative disease or disorder (e.g., including those delineated herein).

In another aspect, the invention relates to a compound of formula A1-14:

A1-14

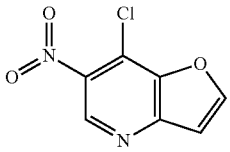

useful for the process of making compounds of formula I.

In another aspect, the invention relates to a process of preparing a compound of formula

I

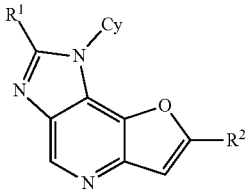

comprising contacting a compound of formula V:

V

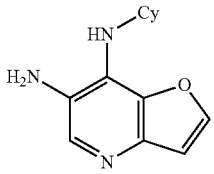

and a compound of formula VI:

VI

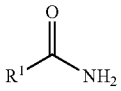

in the presence of a (C$_{1-6}$ alkyl)$_3$oxonium tetrafluoroborate at sufficient temperature, and for sufficient time to produce a compound of formula I:

I

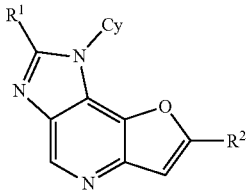

wherein R$^2$ is H, and R$^1$ and Cy are as defined above. The (C$_{1-6}$ alkyl)$_3$oxonium tetrafluoroborate can be triethyloxonium tetrafluoroborate.

In another aspect, the invention relates to a process of preparing compound of formula V comprising reducing a compound of formula VII:

VII

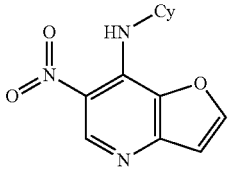

in the presence of a hydrogenation catalyst and hydrogen gas at sufficient temperature, sufficient pressure and for sufficient time to produce a compound of formula V wherein Cy is as defined above. The hydrogenation catalyst can be palladium on carbon.

In another aspect, the invention relates to a process preparing compound of formula VII comprising contacting a compound of formula A1-14:

A1-14

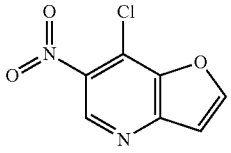

and a compound of formula VIII:

$$Cy\text{-}NH_2 \qquad \text{VIII}$$

in the presence of a base at sufficient temperature, and for sufficient time to produce a compound of formula VII wherein Cy is as defined above. The base can be N,N-Diisopropylethylamine.

DETAILED DESCRIPTION OF THE INVENTION

Definitions

The terms "ameliorate" and "treat" are used interchangeably and both mean decrease, suppress, attenuate, diminish, arrest, or stabilize the development or progression of a disease (e.g., a disease or disorder delineated herein).

By "disease" is meant any condition or disorder that damages or interferes with the normal function of a cell, tissue, or organ.

By "marker" is meant any alteration that is associated with a disease or disorder. For example, any protein or polynucleotide having an alteration in expression level or activity that is associated with a disease or disorder.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

The term "compound" as used herein, is also intended to include pharmaceutically acceptable salts, prodrugs, and prodrug salts of a compound of formulae herein. The term also includes any solvates, hydrates, and polymorphs of any of the foregoing. The specific recitation of "prodrug," "prodrug salt," "solvate," "hydrate," or "polymorph" in certain aspects of the invention described in this application shall not be interpreted as an intended omission of these forms in other aspects of the invention where the term "compound" is used without recitation of these other forms.

A salt of a compound of this invention is formed between an acid and a basic group of the compound, such as an amino functional group, or a base and an acidic group of the compound, such as a carboxyl functional group. According to another preferred embodiment, the compound is a pharmaceutically acceptable acid addition salt.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as amides, esters, carbamates, carbonates, and phosphate analogues. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs".

As used herein and unless otherwise indicated, the term "biohydrolyzable moiety" means a functional group (e.g., amide, ester, carbamate, carbonate, or phosphate analogue, that either: 1) does not destroy the biological activity of the compound and confers upon that compound advantageous properties in vivo, such as uptake, duration of action, or onset of action; or 2) is itself biologically inactive but is converted in vivo to a biologically active compound.

A prodrug salt is a compound formed between an acid and a basic group of the prodrug, such as an amino functional group, or a base and an acidic group of the prodrug, such as a carboxyl functional group. In a one embodiment, the prodrug salt is a pharmaceutically acceptable salt.

Particularly favored prodrugs and prodrug salts are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. Journal of Medicinal Chemistry 1988, 31, 318-322; Bundgaard, H. Design of Prodrugs; Elsevier: Amsterdam, 1985; pp 1-92; Bundgaard, H.; Nielsen, N. M. Journal of Medicinal Chemistry 1987, 30, 451-454; Bundgaard, H. A Textbook of Drug Design and Development; Harwood Academic Publ.: Switzerland, 1991; pp 113-191; Digenis, G. A. et al. Handbook of Experimental Pharmacology 1975, 28, 86-112; Friis, G. J.; Bundgaard, H. A Textbook of Drug Design and Development; 2 ed.; Overseas Publ.: Amsterdam, 1996; pp 351-385; Pitman, I. H. Medicinal Research Reviews 1981, 1, 189-214.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups of prodrugs of this invention include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N, N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

As used herein, the term "polymorph" means solid crystalline forms of a compound or complex thereof which may be characterized by physical means such as, for instance, X-ray powder diffraction patterns or infrared spectroscopy. Different polymorphs of the same compound can exhibit different physical, chemical and/or spectroscopic properties. Different physical properties include, but are not limited to stability (e.g., to heat, light or moisture), compressibility and density (important in formulation and product manufacturing), hygroscopicity, solubility, and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing diastereomers are well known in the art and may be applied as practicable to final compounds or to starting material or intermediates. Other embodiments are those wherein the compound is an isolated compound. The term "at least X % enantiomerically enriched" as used herein means that at least X % of the compound is a single enantiomeric form, wherein X is a number between 0 and 100, inclusive.

The term "stable compounds", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"Stereoisomer" refers to both enantiomers and diastereomers.

As used herein, the term "halo" or "halogen" refers to any radical of fluorine, chlorine, bromine or iodine.

The terms "alk" or "alkyl" refer to straight or branched chain hydrocarbon groups having 1 to 12 carbon atoms, preferably 1 to 8 carbon atoms. The expression "lower alkyl" refers to alkyl groups of 1 to 4 carbon atoms (inclusive).

The term "arylalkyl" refers to a moiety in which an alkyl hydrogen atom is replaced by an aryl group.

The term "alkenyl" refers to straight or branched chain hydrocarbon groups of 2 to 10, preferably 2 to 4, carbon atoms having at least one double bond. Where an alkenyl group is bonded to a nitrogen atom, it is preferred that such group not be bonded directly through a carbon bearing a double bond.

The term "alkoxy" refers to an —O-alkyl radical. The term "alkylenedioxo" refers to a divalent species of the structure —O—R—O—, in which R represents an alkylene.

The term "alkynyl" refers to straight or branched chain hydrocarbon groups of 2 to 10, preferably 2 to 4, carbon atoms having at least one triple bond. Where an alkynyl group is bonded to a nitrogen atom, it is preferred that such group not be bonded directly through a carbon bearing a triple bond.

The term "alkylene" refers to a divalent straight chain bridge of 1 to 5 carbon atoms connected by single bonds (e.g., $—(CH_2)_x—$, wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are $—CH{=}CH—CH{=}CH—$, $—CH_2—CH{=}CH—$, $—CH_2—CH{=}CH—CH_2—$, $—C(CH_3)_2CH{=}CH—$ and $—CH(C_2H_5)—CH{=}CH—$.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are $—C{\equiv}C—$, $—CH_2—C{\equiv}C—$, $—CH(CH_3)C{\equiv}C—$ and $—C{\equiv}C—CH(C_2H_5)CH_2—$.

The terms "cycloalkyl" and "cycloalkenyl" as employed herein includes saturated and partially unsaturated cyclic, respectively, hydrocarbon groups having 3 to 12 carbons, preferably 3 to 8 carbons, and more preferably 3 to 6 carbons.

The terms "Ar" or "aryl" refer to aromatic cyclic groups (for example 6 membered monocyclic, 10 membered bicyclic or 14 membered tricyclic ring systems) which contain 6 to 14 carbon atoms. Exemplary aryl groups include phenyl, naphthyl, biphenyl and anthracene.

"Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system, wherein 0, 1, 2, 3, or 4 atoms of each ring may be substituted by a substituent. Examples, without limitation, of heteroaryl groups are pyrrole, furan, thiophene, imidazole, oxazole, thiazole, pyrazole, pyridine, pyrimidine, quinoline, quinazoline, isoquinoline, purine and carbazole.

The terms "heterocycle", "heterocyclic" or "heterocyclo" refer to fully saturated or partially unsaturated cyclic groups, for example, 3 to 7 membered monocyclic, 7 to 12 membered bicyclic, or 10 to 15 membered tricyclic ring systems, which have at least one heteroatom in at least one ring, wherein 0, 1, 2 or 3 atoms of each ring may be substituted by a substituent. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

The term "heterocyclyl" refers to fully saturated or partially unsaturated cyclic groups, for example, 3 to 7 membered monocyclic, 7 to 12 membered bicyclic, or 10 to 15 membered tricyclic ring systems, which have at least one heteroatom in at least one ring, wherein 0, 1, 2 or 3 atoms of each ring may be substituted by a substituent. Each ring of the heterocyclyl group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclyl group may be attached at any heteroatom or carbon atom of the ring or ring system.

The term "substituents" refers to a group "substituted" on any functional group delineated herein, e.g., alkyl, alkenyl, alkynyl, cycloalkyl, cycloalkenyl, aryl, heterocyclyl, or heteroaryl group at any atom of that group. Suitable substituents include, without limitation halogen, CN, $NO_2$, $OR^{15}$, $SR^{15}$, $S(O)_2OR^{15}$, $NR^{15}R^{16}$, $C_1$-$C_2$ perfluoroalkyl, $C_1$-$C_2$ perfluoroalkoxy, 1,2-methylenedioxy, $C(O)OR^{15}$, $C(O)NR^{15}R^{16}$, $OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)R^{17}$, $NR^{15}C(O)R^{17}$, $S(O)R^{17}$, $S(O)_2R^{17}$, $R^{16}$, oxo, $C(O)R^{16}$, $C(O)(CH_2)nOH$, $(CH_2)nOR^{15}$, $(CH_2)nC(O)NR^{15}R^{16}$, $NR^{15}S(O)_2R^{17}$, where n is independently 0-6 inclusive. Each $R^{15}$ is independently hydrogen, $C_1$-$C_4$ alkyl or $C_3$-$C_6$ cycloalkyl. Each $R^{16}$ is independently hydrogen, alkenyl, alkynyl, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $C_3$-$C_6$ cycloalkyl, aryl, heterocyclyl, heteroaryl and $C_1$-$C_4$ alkyl in each $R^{15}$, $R^{16}$ and $R^{17}$ can optionally be substituted with halogen, CN, $C_1$-$C_4$ alkyl, OH, $C_1$-$C_4$ alkoxy, $NH_2$, $C_1$-$C_4$ alkylamino, $C_1$-$C_4$ dialkylamino, $C_1$-$C_2$ perfluoroalkyl, $C_1$-$C_2$ perfluoroalkoxy, or 1,2-methylenedioxy.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The compounds of this invention may contain one or more asymmetric centers and thus occur as racemates and racemic mixtures, single enantiomers, individual diastereomers and diastereomeric mixtures, as well as cis and trans geometric isomers. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention.

Compounds of the Invention

In one aspect, the present invention provides a compound of Formula I:

I

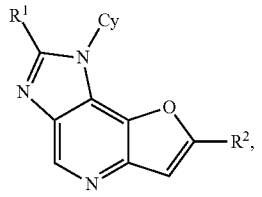

or a pharmaceutically acceptable salt thereof; or a prodrug, or a pharmaceutically acceptable salt of a prodrug thereof; or a hydrate, solvate, or polymorph thereof; wherein:

$R^1$ is H, halo, or $C_{1-3}$ alkyl optionally substituted with 1, 2, or 3 substituents independently selected from the group consisting of halo, OH, CN, OR, NHR, NRR', N(R)C(=O)R', N(R)C(=O)(O)R', OC(=O)NRR', C(=O)R, C(=O)NRR', $N(R)S(O)_2R'$, $S(O)_2R$, and $S(O)_2NRR'$;

$R^2$ is H, halo, or $C_{1-3}$ alkyl;

Cy is $C_{3-7}$ cycloalkyl, 3-7 membered heterocyclyl, phenyl, or 5-6 membered heteroaryl, each optionally substituted with 1, 2, or 3 substituents independently selected from the group consisting of $R^3$, oxo, halo, OH, CN, OR, NHR, NRR', N(R)C(=O)R', N(R)C(=O)(O)R', OC(=O)NRR', C(=O)R, C(=O)NRR', $N(R)S(O)_2R'$, $S(O)_2R$, and $S(O)_2NRR'$, wherein $R^3$ is $C_{1-3}$ alkyl optionally substituted with 1, 2, or 3 substituents independently selected from the group consisting of halo, OH, CN, OR, NHR, NRR', N(R)C(=O)R', N(R)C(=O)(O)R', OC(=O)NRR', C(=O)R, C(=O)NRR', $N(R)S(O)_2R'$, $S(O)_2R$, and $S(O)_2NRR'$;

R, R' each is independently H, or $C_{1-3}$ alkyl optionally substituted with 1, 2, or 3 substituents independently selected from the group consisting of halo, OH, and CN.

In another aspect Cy can be $C_{5-7}$ cycloalkyl, or 5-7 membered heterocyclyl, each optionally substituted with 1, 2, or 3 substituents independently selected from the group consisting of $R^3$, oxo, halo, OH, CN, OR, NHR, NRR', N(R)C(=O)R', N(R)C(=O)(O)R', OC(=O)NRR', C(=O)R, C(=O)NRR', N(R)S(O)$_2$R', S(O)$_2$R, and S(O)$_2$NRR', wherein $R^3$ is $C_{1-3}$ alkyl optionally substituted with 1, 2, or 3 substituents independently selected from the group consisting of halo, OH, CN, OR, NHR, NRR', N(R)C(=O)R', N(R)C(=O)(O)R', OC(=O)NRR', C(=O)R, C(=O)NRR', N(R)S(O)$_2$R', S(O)$_2$R, and S(O)$_2$NRR'.

In another aspect $R^2$ can be hydrogen.

Representative compounds of the invention are depicted in Table 1. In these examples the stereochemistry at the chiral carbon atoms is independently either RS, R, or S, unless specified. For compounds 4, 7-11, the stereochemistry shows only one of the trans or cis isomers, and the structures of their respective isomers are not shown. The structures depicted herein, including the Table 1 structures, may contain certain —NH—, —NH$_2$ (amino) and —OH (hydroxyl) groups where the corresponding hydrogen atom(s) do not explicitly appear; however they are to be read as —NH—, —NH$_2$ or —OH as the case may be. In certain structures, a stick bond is drawn and is meant to depict a methyl group.

TABLE 1

1

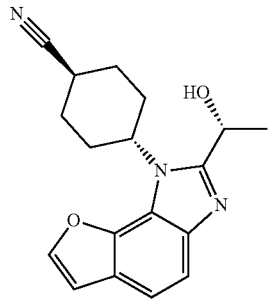

2

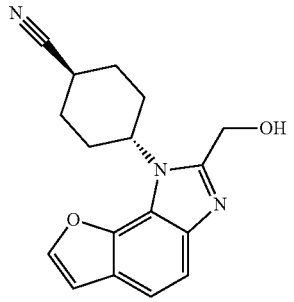

3

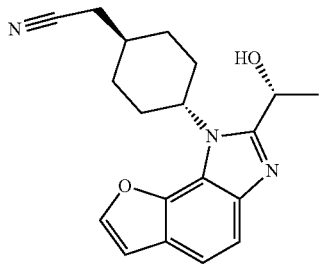

TABLE 1-continued

4

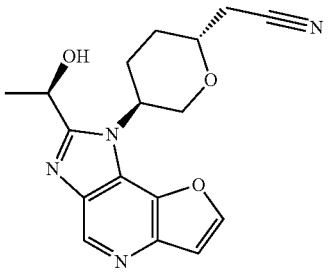

5

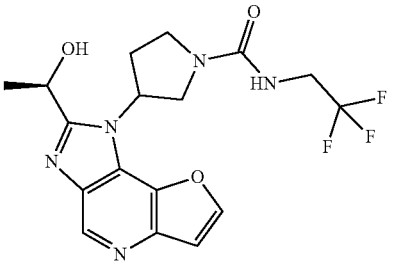

6

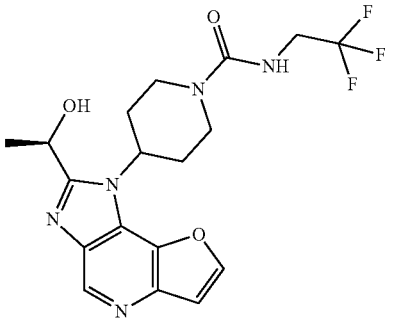

7

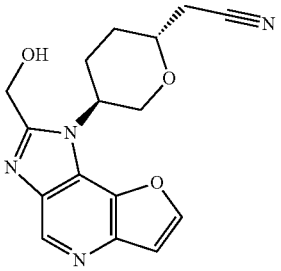

8

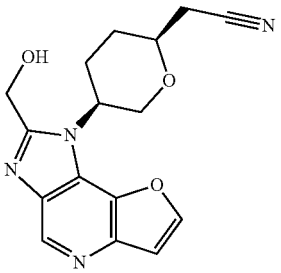

TABLE 1-continued

| | |
|---|---|
| 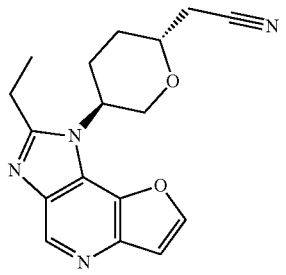 | 9 |
| 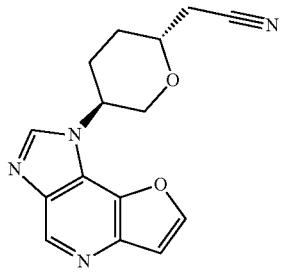 | 10 |
| 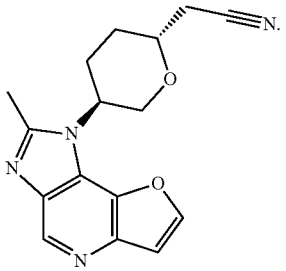 | 11 |

Representative compounds of the invention are listed below:

trans-4-[2-[(R)-1-Hydroxyethyl]-1H-furo[3,2-b] imidazo[4,5-d]pyridin-1-yl]cyclohexanecarbonitrile (1);

trans-4-[2-(Hydroxymethyl)furo[3,2-b]imidazo[4,5-d]pyridin-1-yl]cyclohexanecarbonitrile (2);

2-[trans-4-[2-[(R)-1-Hydroxyethyl]furo[3,2-b]imidazo[4,5-d]pyridin-1-yl]cyclohexyl]acetonitrile (3);

2-[(2R,5S)-5-[2-[(R)-1-Hydroxyethyl]furo[3,2-b]imidazo[4,5-d]pyridin-1-yl]tetrahydropyran-2-yl]acetonitrile (4);

3-[2-[(R)-1-Hydroxyethyl]-1H-furo[3,2-b]imidazo[4,5-d]pyridin-1-yl]-N-(2,2,2-trifluoroethyl)pyrrolidine-1-carboxamide (5);

(R)-4-[2-(1-Hydroxyethyl)-1H-furo[3,2-b]imidazo[4,5-d]pyridin-1-yl]-N-(2,2,2-trifluoroethyl)piperidine-1-carboxamide (6);

2-[(2R,5 S)-5-[2-(Hydroxymethyl)furo[3,2-b]imidazo[4,5-d]pyridin-1-yl]tetrahydropyran-2-yl]acetonitrile (7);

2-[(2S,5 S)-5-[2-(Hydroxymethyl)furo[3,2-b]imidazo[4,5-d]pyridin-1-yl]tetrahydropyran-2-yl]acetonitrile (8), 2-[(2R,5S)-5-[2-Ethylfuro[3,2-b]imidazo[4,5-d] pyridin-1-yl] tetrahydropyran-2-yl]acetonitrile (9), 2-[(2R,5S)-5-[2-Furo[3,2-b]imidazo[4,5-d] pyridin-1-yl] tetrahydropyran-2-yl]acetonitrile (10), 2-[(2R,5S)-5-[2-Methylfuro[3,2-b]imidazo[4,5-d] pyridin-1-yl] tetrahydropyran-2-yl]acetonitrile (11).

The synthesis of compounds of the formulae herein can be readily effected by synthetic chemists of ordinary skill. Relevant procedures and intermediates are disclosed, for instance, herein. Each of the patents, patent applications, and publications, whether in traditional journals or available only through the internet, referred to herein, is incorporated in its entirety by reference.

Other approaches to synthesizing compounds of the formulae herein can readily be adapted from references cited herein. Variations of these procedures and their optimization are within the skill of the ordinary practitioner.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (e.g., $R^1$, $R^2$, R, R', X, etc.) or not. The suitability of a chemical group in a compound structure for use in synthesis of another compound structure is within the knowledge of one of ordinary skill in the art. Additional methods of synthesizing compounds of the formulae herein and their synthetic precursors, including those within routes not explicitly shown in schemes herein, are within the means of chemists of ordinary skill in the art. Methods for optimizing reaction conditions, if necessary minimizing competing by-products, are known in the art. The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, Comprehensive Organic Transformations, VCH Publishers (1989); T. W. Greene and P. G. M. Wuts, Protective Groups in Organic Synthesis, 3rd Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, sublimation, crystallization, trituration, solid phase extraction, and chromatography).

Combinations of substituents and variables envisioned by this invention are only those that result in the formation of stable compounds.

The invention also provides compositions comprising an effective amount of a compound of any of the formulae herein, or a pharmaceutically acceptable salt, solvate, hydrate, polymorph or prodrug, if applicable, of said compound; and an acceptable carrier. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US patents, some of which include, but are not limited to, U.S. Pat. Nos. 4,369,172; and 4,842,866, and references cited therein. Coatings can be used for delivery of compounds to the intestine (see, e.g., U.S. Pat. Nos. 6,638,534, 5,217,720, and 6,569,457, 6,461,631, 6,528,080, 6,800,663, and references cited therein). A useful formulation for the compounds of this invention is the form of enteric pellets of which the enteric layer comprises hydroxypropylmethyl cellulose acetate succinate.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. Journal of Medicinal Chemistry 1988, 31, 318-322; Bundgaard, H. Design of Prodrugs; Elsevier: Amsterdam, 1985; pp 1-92; Bundgaard, H.; Nielsen, N. M. Journal of Medicinal Chemistry 1987, 30, 451-454; Bundgaard, H. A Textbook of Drug Design and Development; Harwood Academic Publ.: Switzerland, 1991; pp 113-191; Digenis, G. A. et al. Handbook of Experimental Pharmacology 1975, 28, 86-112; Friis, G. J.; Bundgaard, H. A Textbook of Drug Design and Development; 2 ed.; Overseas Publ.: Amsterdam, 1996; pp 351-385; Pitman, I. H. Medicinal Research Reviews 1981, 1, 189-214.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

In another embodiment, a composition of the present invention further comprises a second therapeutic agent. The second therapeutic agent includes any compound or therapeutic agent known to have or that demonstrates advantageous properties when administered alone or with a compound of any of the formulae herein. Drugs that could be usefully combined with these compounds include other kinase inhibitors and/or other therapeutic agents for the treatment of the diseases and disorders discussed above.

Such agents are described in detail in the art. Preferably, the second therapeutic agent is an agent useful in the treatment or prevention of a disease or condition selected from cancer and neoplastic diseases or disorders, or autoimmune and inflammatory diseases or disorders.

In another embodiment, the invention provides separate dosage forms of a compound of this invention and a second therapeutic agent that are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardley, N.Y., 1970, 537. An effective amount of a compound of this invention can range from about 0.001 mg/kg to about 500 mg/kg, more preferably 0.01 mg/kg to about 50 mg/kg, more preferably 0.1 mg/kg to about 2.5 mg/kg. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

According to another embodiment, the invention provides a method of treating a subject suffering from or susceptible to a disease or disorder or symptom thereof (e.g., those delineated herein) comprising the step of administering to said subject an effective amount of a compound or a composition of this invention. Such diseases are well known in the art and are also disclosed herein.

In one aspect, the method of treating involves treatment of a disorder that is mediated by the Jak1 protein kinase.

In another aspect, the method of treating involves treatment of a disorder that is mediated primarily by the Jak1 protein kinase, but also to some extent by the Jak2 protein kinase.

In another aspect, the invention provides a method of treating a disease in a subject comprising administering to the subject a compound of any of the formulae herein.

In another aspect, invention provides a method of treating a disease in a subject comprising administering to the subject a composition comprising a compound of any of the formulae herein.

In another aspect, invention provides a method of treating a disease in a subject comprising administering to the subject a composition comprising a compound of any of the formulae herein.

In certain embodiments, the disease is mediated by the Jak1 kinase. For example, the condition may be an inflammatory disease/disorder, an autoimmune disease/disorder, such as, but not limited to rheumatoid arthritis (RA), juvenile idiopathic arthritis, osteoarthritis, multiple sclerosis, allergic asthma, chronic obstructive pulmonary disease, bronchitis, experimental allergic encephalomyelitis, Crohn's disease, vasculitis, cardiomyopathy, ankylosing spondylitis (AS), glomerulonephritis, insulin-dependent diabetes, psoriatic arthritis, psoriasis, plaque psoriasis, ulcerative colitis, systemic lupus erythematosus (SLE), diabetic nephropathy, peripheral neuropathy, uveitis, fibrosing alveolitis, type I diabetes, juvenile diabetes, Castleman disease, neutropenia, endometriosis, autoimmune thyroid disease, sperm and testicular autoimmunity, scleroderma, axonal & neuronal neuropathies, allergic rhinitis, sinusitis, hemolytic anemia, Graves, disease, Hashimoto's thyroiditis, IgA nephropathy, amyloidosis, Behcet's disease, sarcoidosis, vesiculobullous dermatosis, myositis, dry eye syndrome, primary biliary cirrhosis, polymyalgia rheumatic, Reiter's syndrome, autoimmune immunodeficiency, Chagas disease, Kawasaki syndrome, celiac sprue, myasthenia gravis, Sjogren's Syndrome, alopecia areata, vitiligo, atopic dermatitis, POEMS syndrome, lupus, inflammatory bowel disease, chronic obstructive pulmonary disease (COPD), pemphigus vulgris, bullous pemphigoid, chronic fatigue syndrome, organ transplant rejection (e.g., allograft rejection and graft versus host disease), viral diseases such as Epstein Barr virus, Hepatitis C, HIV, HTLV 1, Varicella-Zoster virus, and human papilloma virus, gouty arthritis, septic or infectious arthritis, reactive arthritis, reflext sympathetic dystrophy, algodystrophy, Tietze syndrome, costal athropathy, Mseleni disease, Handigodu disease, fibromyalgia, scleroderma, congentital cartilage malformations, and pulmonary arterial hypertension.

Further JAK-associated diseases include inflammation and inflammatory diseases or disorders, Examples include sarcoidosis, inflammatory diseases of the eye (e.g., iritis, uveitis, scleritis, conjunctivitis, blepharitis, or related disease), inflammatory diseases of the respiratory tract (e.g., the upper respiratory tract including the nose and sinuses such as rhinitis or sinusitis or the lowe respiratory tract including bronchitis, chronic obstructive pulmonary disease, and the like), inflammatory myopathy such as myocarditis and other inflammatory diseases.

In another embodiment, the disease is, cancer, a proliferative or other neoplastic disease, such as, but not limited to, breast cancer, Castleman's disease, colon and colorectal cancers, gastric cancer, gastrointestinal carcinoid tumor, gastrointestinal stromal tumor, glioblastoma, head and neck cancer, Kaposi's sarcoma, liver cancer, lung cancer, melanoma, pancreatic cancer, prostate cancer, renal cancer, rectal cancer, small intestine cancer, thyroid cancer, uterine leiomyosarcoma, lymphomas and leukemias such as acute lymphoblastic leukemia, acute myelogenous leukemia, multiple myeloma, cutaneous T cell lymphoma, cutaneous B cell lymphoma, myelodysplastic syndrome (MDS), myeloproliferative disorders (MPDs) such as polycythemia vera (PV), essential thrombocythemia (ET), myelofibrosis with myeloid metaplasia (MMM), primary myelofibrosis (PMF), chronic myelogenous leukemia (CML), chronic myelomonoytic leukemia (CMML), hypereosinophilic syndrome (HES), systemic mast cell disease (SMCD). In some embodiments, the myeloproliferative disorder is post-essential thrombocythemia melofibrosis (Post-ET MF) or post-polycythemia versa myelofibrosis (Post-PV MF), Further JAK-associated diseases include ischemia reperfusion injuries or a disease or condition related to an inflammatory ischemic event such as stroke or cardiac arrest, endotoxin-driven disease state (e.g., complications after bypass surgery of chronic endotoxin states contributing to chronic cardiac failure), anorexia, sclerodermitis, fibrosis, conditions associated with hypoxia or astrogliosis such as diabetic retinopathy, cancer, or neurodegeneration, and other inflammatory disease such as systemic inflammatory response syndrome and septic shock.

Other JAK-associated disease include gout and increased prostate size due to, e.g., benign prostate hypertrophy or benign prostatic hyperplasia, as well as bone resorption diseases such as osteoporosis or osteoarthritis, bone resorption diseases associated with: hormonal imbalance and/or hormonal therapy, autoimmune disease (e.g., osseous sarcoidosis).

Other examples of JAK-associated diseases or conditions include ameliorating the dermatological side effects of other pharmaceuticals by administration of the compound of the invention. For example, numerous pharmaceutical agents result in unwanted allergic reaction which can manifest as acneiform rash or related dermatitis. Example pharmaceutical agents that have such undesirable side effects include anti-cancer drugs such as gefitinib, cetuximab, erlotinib, and the like. The compounds of the invention may be administered systemically or topically (e.g., localized to the vicinity of the dermatitis) in combination with pharmaceutical agent having the undesirable dermatological side effect. Accordingly, compositions of the invention include topical formulations containing the compound of the invention and a further pharmaceutical agent which can cause dermatitis, skin disorders, or related side effects.

In a one embodiment, the method of this invention is used to treat a subject suffering from or susceptible to a disease or condition. Such diseases, disorders or symptoms thereof include, for example, those modulated by the Jak1 protein kinase. The disease or disease symptom can be, for example, rheumatoid arthritis, cancer or proliferation disease or disorder. Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In yet another embodiment, the compounds of the formulae herein (and compositions thereof) can be used to treat subjects having a disease or disorder who have been treated with and developed resistance to other therapeutic agents. In one aspect, the methods herein include those where a subject resistant to treatment with methotrexate or anti-TNF-alpha therapy.

In another embodiment, the invention provides a method of modulating the activity of the Jak1 protein kinase in a cell comprising contacting a cell with one or more compounds of any of the formulae herein.

In another embodiment, the above method of treatment comprises the further step of co-administering to said patient one or more second therapeutic agents. The choice of second therapeutic agent may be made from any therapeutic agent known to be useful for indications herein. One or more additional therapeutic may include chemotherapeutics, anti-inflammatory agents, steroids, immunosuppressants, as well as PI3Kdelta, mTOR, BCR-ABl, FLT-3, RAF and FAK kinase inhibitors, and the like. Additional therapeutic agents include but are not limited to agents for treatment of diseases, disorders or symptoms thereof including for example, (1) agents that modulate human immune system or are anti-inflammatory agents selected from the group consisting of, but not limited to, aspirin, acetaminophen, aminosalicylate, antithymoyte globulin, ciprofloxacin, corticosteroid, cyclosporine, deoxyspergualin, daclizuma, metronidazole, probiotic, tacrolimus, ibuprofen, naproxen, piroxicam, prednisolone, dexamethasone, anti-inflammatory steroid, methotrexate, chloroquine, azathioprine, hydroxychloroquine, mycophnolate, muromonab-CD3, penicillamine, sulfasalazine, leflunomide, tacrolimus, tocilzumab, anakinra, abatacept, certolizumab pegol, golimumab, rapamycin, vedolizumab, natalizumab, ustekinumab, rituximab, efalizumab, belimumab, etanercept, infliximab, adalimuman, immune modulator (e.g., activator) for CD4+ CD25+ regulatory T cells, NSAIDs, analgesics, other non-biological disease-modifying anti-rheumatic drugs (DMARDs) and/or in combination with anti-TNF-alpha biological agents such as TNA antagnoists like chimeric, humanized or human TNF antibodies, adalimumab, infliximab, golimumab, CDP571 and soluble p55 or l75 TNA receptors, derivatives, thereof, etanerceptr pr lenercept (2) anti-cancer and anti-neoplastic agents, antiproliferative agents, antineoplastic agents, antitumor agents, antimetabolite-type/thymidilate synthase inhibitor antineoplastic agents, alkylating-type antineoplastic agents, antibiotic-type antineoplastic agents, or, any other agent typically administered as a primary or adjuvant agent in cancer treatment protocols (e.g., antinausea, antianemia, etc.), including for example, vinblastine sulfate, vincristine, vindesine, vinestramide, vinorelbine, vintriptol, vinzolidine, tamoxifen, toremifen, raloxifene, droloxifene, iodoxyfene, megestrol acetate, anastrozole, letrazole, borazole, exemestane, flutamide, nilutamide, bicalutamide, cyproterone acetate, goserelin acetate, luprolide, finasteride, herceptin, methotrexate, 5-fluorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, vincristine, taxol, taxotere, etoposide, teniposide, amsacrine, irinotecan, topotecan, an epothilone, Iressa, Avastin, OSI-774, angiogenesis inhibitors, EGFR inhibitors, MEK inhibitors, VEGFR inhibitors, CDK inhibitors, Her1 and Her2 inhibitors, monoclonal antibodies, proteosome inhibitors such as bortezomib, thalidomide, and revlimid; an apoptotic inducer such as ABT-737. A nucleic acid therapy such as antisense or RNAi; nuclear receptor ligands (e.g., agonists and/or antagonists. All-trans retinoic acid or boxarotene); epigenetic targeting agents such as histone deacetylase inhibitors (e.g., vorinostat), hypomethylating agents (e.g., decitabine), regulators of protein stability such as HSP90 inhibitors, ubiquitin and/or ubiquitin like conjugating or deconjugating molecules.

In some embodiments, the additional pharmaceutical agent is selected from IMiDs, an anti-IL-6 agent, an anti-TNF-alpha agent, a hypomethylating agent, and a biologic response modifier (RBM). RBM is generally a substance made from living organisms to treat disease. Examples of RBMs include IL-2, GM-CSF, CSF, monoclonal antibodies such as abciximab, etanercept, infliximab, rituximab, trastuzumab, and high dose ascorbate. The hypomethylating agent is a DNA methyltransferase inhibitor such as 5 azacytidine and decitabine. Examples of IMiDs include thalidomide, lenalidomide, pomalidomide, CC-11006, and CC-10015.

In some embodiments, the additional pharmaceutical agents include anti-thymocyte globulin, recombinant human granulocyte colony-stimulating factor (G-CSF), granulocyte-moncyte CSF (GM-CSF), a erythropoiesis-stimulating agent (ESA), and cyclosporine.

In some embodiments, the additional therapeutic agent is an additional JAK inhibitor. In some embodiments, the additional JAK inhibitor is tofacitinib, ruxolitinib or baricitinib.

In some embodiments, one or more JAK inhibitors of the invention can be used in combination with one or more other cancer therapeutic agents in the treatment of cancer, such as multiple myeloma, and may improve the treatment benefit as compared to the benefit shown by the other cancer therapeutic agents, without exacerbating of their toxic effects. Examples of additional pharmaceutical agents used in the treatment of multiple myeloma can include, without limition, melphalan, melphalan plus prednisone (MP), doxorubicin, dexamethasone, and bortezomib. Additional agents used in the treatment of multiple myeoloma include BRC-ABL, FLT-3, RAF, MEK, PI3K, mTOR inhibitors. Additive or synergistic effects are desirable outcomes of combining a JAK inhibitor of the current invention with an additional agent.

Furthermore, resistance of multiple myeloma cells to agents such as dexamethasone or other agents may be reversible upon treatment with a JAK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK inhibitor of the invention where the dexamethasone is administered intermittently as opposed to continuously.

In some embodiments, combinations of one or more JAK inhibitors of the invention with other therapeutic agents can be administered to a patient prior to, during, and/or after a bone marrow transplantation or stem cell transplantation.

In some embodiments, the additional therapeutic agent is fluocinolone acetonide or remexolone.

In some embodiments, the additional therapeutic is a corticosteroid such as triamcinolone, dexamethasone, fluocinolone, cortisone, prednisolone, or flumetholone.

In some embodimennts, the additional therapeutic agent includes Dehydrex, Civamide, sodium hyaluronate, cyclosporine, ARG101, AGR1012, ecabet sodium, gefarnate, 15-(s)-hydroxyeicosatetraenoic acid, cevilemine doxycycline, minocycline, iDestrin, cyclosporine A, oxytetracycline, voclosporin, ARG103, RX-10045, DYN15, rivoglitazone, TB4, OPH-01, PCS101, REV1-31, Lacritin, rebamipide, OT-551, PAI-2, pilocarpine, tacrolimus, pimercrolimus, loteprednol etabonate, rituximan, diquafosol tetrasodium, KLS-0611, dehydroepiandrosterone, anakinra, efalizuma, mycophenolate sodium, etanercept, hydroxychloroquine, NGX267, actemra, or L-asparaginase.

In some embodiments, the additional therapeutic agent is an anti-angiogenic agent, cholinergic agent, TRP-1 receptor modulator, a calcium channel blocker, a mucin secretagogue, MUC1 stimulant, a calcineurin inhibitor, a P2Y2 receptor agonist, a muscarinic receptor agonist, and a tetracycline derivative.

In some embodimenbts, the additional therapeutic agents include demulcent eye drops, which include, but not limited to, compositions containing polyvinylalchol, hyroxypropyl methylcellulose, glycerin, polyethylene glycol (e.g., PEG400), or carboxymethyl cellose, In some embodiments, the additional therapeutic agent is a mucolytic drug, such as N-acetyl-systeine, which can interact with the mucoproteins and decrease the viscositiy of the tear film.

In some embodiments, the additional therapeutic agent includes an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin, vanocomycin; tetracyclines; rifampin and its derivatives; cycloserine; beta-lactams; cephalosporins; emphotericins; fluconazole; flucytosine; natamycin; miconazole; ketoconazole; corticosteroids; dicloenac; flurbiprofen; ketorolac; suprofen; cromolyn; iodoxamide; levocabastin; naphazoline; antazoline; pheniramine; or azalide antibiotic.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention comprising both a compound of the invention and a second therapeutic agent to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of any of the formulae herein alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of the formulae herein for use in the treatment or prevention in a subject of a disease, disorder or symptom thereof delineated herein.

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is prescreened or identified as in need of such treatment by assessment for a relevant marker or indicator of suitability for such treatment.

In one embodiment, the invention provides a method of monitoring treatment progress. The method includes the step of determining a level of diagnostic marker (Marker) (e.g., any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radiolabelling/assay techniques, blotting/chemiluminescence methods, real-time PCR, and the like.

The present invention also provides kits for use to treat diseases, disorders, or symptoms thereof, including those delineated herein. These kits comprise: a) a pharmaceutical composition comprising a compound of any of the formula herein or a pharmaceutically acceptable salt thereof; or a prodrug, or a pharmaceutically acceptable salt of a prodrug thereof; or a hydrate, solvate, or polymorph thereof, wherein said pharmaceutical composition is in a container; and b) instructions describing a method of using the pharmaceutical composition to treat the disease, disorder, or symptoms thereof, including those delineated herein.

The container may be any vessel or other sealed or sealable apparatus that can hold said pharmaceutical composition. Examples include bottles, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. Preferably, the container is a blister pack.

The kit may additionally comprising information and/or instructions for the physician, pharmacist or subject. Such memory aids include numbers printed on each chamber or division containing a dosage that corresponds with the days of the regimen which the tablets or capsules so specified should be ingested, or days of the week printed on each chamber or division, or a card which contains the same type of information.

The compounds delineated herein can be assessed for their biological activity using protocols known in the art, including for example, those delineated herein. Certain of the compounds herein demonstrate unexpectedly superior attributes (e.g., inhibition of P450, metabolic stability, pharmacokinetic properties, etc.) making them superior candidates as potential therapeutic agents.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

EXAMPLES

Example 1: Synthesis of trans-4-[2-[(R)-1-Hydroxyethyl]-1H-furo [3,2-b]imidazo [4,5-d]pyridin-1-yl] cyclohexanecarbonitrile (1)

1

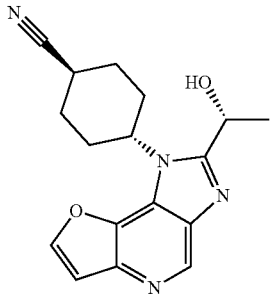

Scheme 1

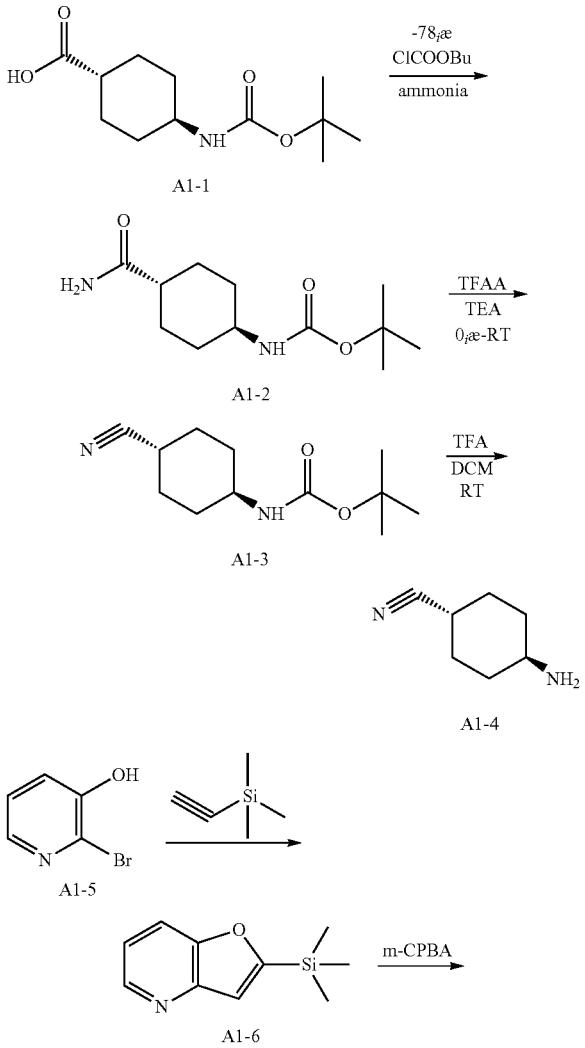

-continued

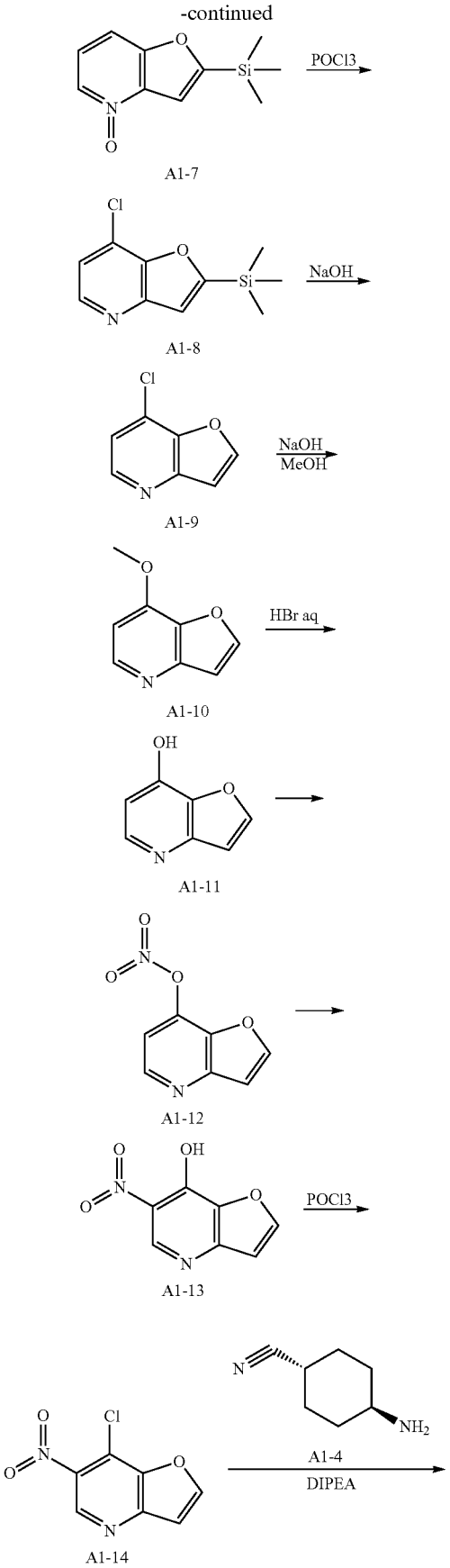

-continued

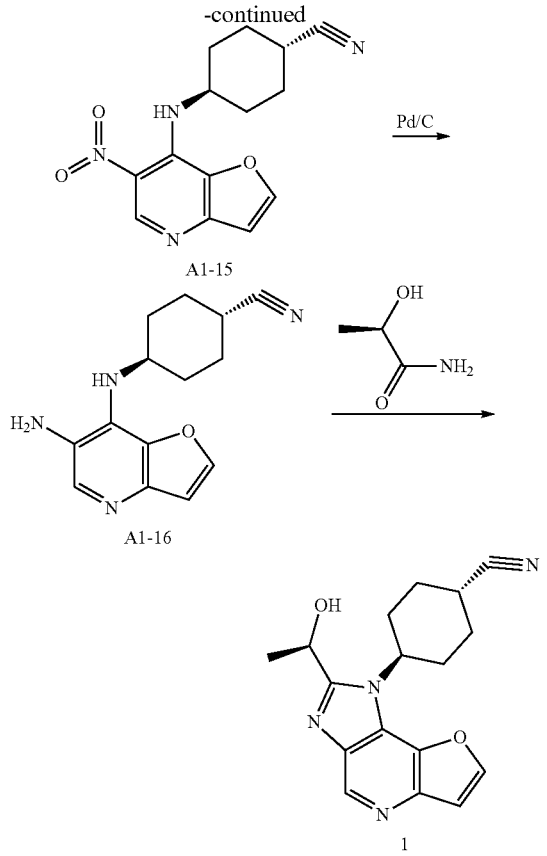

Step 1. A solution of trans-4-(Boc-amino)cyclohexane carboxylic acid (A1-1) (62 g, 0.256 mol, 1.0 eq) in THF (1500 mL) was treated with NMM (64.6 g, 0.64 mol, 2.5 eq) in nitrogen atmosphere. The mixture was cooled to −78° C., and isobutyl chloroformate (33.6 g, 0.33 mol, 1.3 eq) was added dropwise. After stirring at −78° C. for 1 hr, $NH_3$(gas) was bubbled through the mixture for about 20 mins. After that the reaction temperature rose to −30° C., then stirring at −30° C. for 1 hr. The resulting slurry was filtered, washed by water (3*200 mL), and oven dried to give compound A1-2 as white powder (58 g, yield 93.5%). MS-ESI:$[M+1]^+$: 243.1

$^1$H NMR (300 MHz, $d_6$-DMSO): 7.192 (s, 1H), 6.688-6.728 (m, 2H), 3.122-3.147 (m, 1H), 1.92-1.959 (m, 1H), 1.696-1.787 (m, 4H), 1.382 (s, 9H), 1.086-1.358 (m, 4H).

Step 2. A solution of compound A1-2 (74 g, 0.306 mol, 1.0 eq) in DCM (1000 mL) was treated with triethylamine (77.2 g, 0.64 mol, 2.5 eq). The mixture was cooled to 0° C. in ice-bath, and TFAA (80.9 g, 0.383 mol, 1.25 eq) was added dropwise. The ice bath was removed after addition and the reaction temperature rose to 20° C., then stirring at 20° C. for 2 hrs, water (300 mL) was added, and then the aqueous phase was extracted twice with DCM. The combined extracts was washed with brine, dried over anhydrous sodium sulfate, concentrated and purified by silica gel column chromatography to give compound A1-3 as white powder (46 g, yield 67.1%). MS-ESI:$[M+1]^+$: 225.1.

$^1$H NMR (300 MHz, $CDCl_3$): 4.397 (m, 1H), 3.467 (m, 1H), 2.381-2.418 (m, 1H), 2.079-2.147 (m, 4H), 1.613-1.757 (m, 2H), 1.454 (s, 9H), 1.114-1.232 (m, 2H).

Step 3. To a solution of compound A1-3 (10 g, 44.6 mmol, 1.0 eq) in DCM (50 mL), was added TFA (20 g). The reaction mixture was stirred for 2 hrs at room temperature until TLC showed the reaction was complete, then concentrated under vacuum. Ice-water (30 mL) was added and the solution was treated with aqueous sodium hydroxide solution (4 mol/L) to pH 10. Then the aqueous phase was extracted six times with DCM/methanol (10/1). The combined extracts was dried over anhydrous sodium sulfate, concentrated to give compound A1-4 as an off-white solid (5.1 g, yield 91.9%). MS-ESI:$[M+1]^+$: 125.1.

$^1$H NMR (300 MHz, $CDCl_3$): 2.738-2.772 (m, 1H), 2.370-2.421 (m, 1H), 2.115-2.170 (m, 2H), 1.923-1.977 (m, 2H), 1.580-1.694 (m, 2H), 1.075-1.197 (m, 2H)

Step 4. In nitrogen atmosphere, to a solution of 2-Bromo-3-hydroxypyridine (A1-5) (225 g, 1.293 mol, 1.0 eq), trimethylsilylacetylene (153.3 g, 1.592 mol, 1.23 eq) in 1,4-dioxane (2500 mL) was added CuI (25 g) and $Pd(PPh3)_2Cl_2$ (45 g). The reaction mixture was stirred for 30 mins at 25° C., then cooled to 10° C. and triethylamine (363 g, 3.594 mol, 2.78 eq) was added dropwise. After stirring for 4 hrs at 60° C., the solution was cooled and concentrated under vacuum. The residue was added water (2000 mL) and MTBE (200 mL), stirring and filtered. The filtrate was extracted with MTBE (1000 mL*2). The combined organic layers was washed with brine, dried over anhydrous sodium sulfate, concentrated and purified by silica gel column chromatography to give compound A1-6 as light brown liquid (150 g, yield 60.7%). GC-MS: 191 (EI)

Step 5. To a solution of compound A1-6 (105 g, 0.55 mol, 1.0 eq) in DCM (1000 mL) was added m-chloroperoxybenzoic acid (85%, 230 g, 1.13 mol, 12.06 eq) in portions below 25° C. After stirring overnight at room temperature, saturated sodium bicarbonate solution was added to pH 7-8 in ice-bath. The resulting mixture was filtered, and the filtrate was separate, and was extracted twice with DCM. The combined organic layers was washed with saturated sodium bicarbonate solution and brine, dried over anhydrous sodium sulfate, concentrated to give compound A1-7 as a brown liquid (115 g, yield 100%).

Step 6. A solution of compound A1-7 (115 g, 0.55 mol, 1.0 eq) in toluene (400 mL) was added to phosphorus oxychloride (400 mL) in ice-bath below 30° C. The reaction mixture was stirred for 2 hrs at 90° C., cooled to room temperature, and concentrated. The residue was slowly added saturated sodium bicarbonate solution to pH 7-8 below 20° C., and the mixture was extracted twice with MTBE. The combined organic layers was washed with brine, dried over anhydrous sodium sulfate, concentrated and purified by silica gel column chromatography to give compound A1-8 as a yellow liquid (73 g, yield 58.7%). GC-MS: 225 (EI)

Step 7. To a solution of compound A1-8 (73 g, 0.323 mol, 1.0 eq) in THF (400 mL) was added aqueous sodium hydroxide solution (300 mL, 4 mol/L). After stirring for 1 hr at 50° C., the reaction mixture was cooled to room temperature and 1000 mL water was added. The mixture was extracted twice with MTBE. The combined organic layers was washed with brine, dried over anhydrous sodium sulfate, concentrated and recrystallized from ethyl acetate and petroleum ether to give compound A1-9 as an off-white powder (30 g, yield 60.5%). GC-MS: 153 (EI)

$^1$H NMR (300 MHz, $CDCl_3$): 8.485 (d, 1H), 7.945 (d, 1H), 7.312 (d, 1H), 7.079 (d, 1H).

Step 8. Compound A1-9 (9.21 g, 60 mmol, 1.0 eq) was dissolved in methanol (150 mL), then water (150 mL) and sodium hydroxide (24 g, 10 eq) were added. After stirring for 1 hr at 50° C., the reaction mixture was cooled to 20° C. and concentrated. The residue was extracted three times with DCM, then the combined organic layers was dried over anhydrous sodium sulfate and concentrated to give compound A1-10 as a yellow liquid (5.5 g, yield 61.5%). MS-ESI:$[M+1]^+$: 150

Step 9. Compound A1-10 (5.5 g, 37 mmol, 1.0 eq) was added to 40% HBr aq (150 mL). The reaction mixture was heated to reflux for 18 hrs, cooled and concentrated. The residue was treated with saturated sodium bicarbonate solution (100 mL) to pH 7-8. After stirring for 20 min, the precipitate was filtered, washed with water, and oven dried to give compound A1-11 as an off-white powder (3.1 g, yield 62%). MS-ESI:$[M+1]^+$: 136

Step 10. In nitrogen atmosphere, a mixture of compound A1-11 (1.68 g, 12.4 mmol, 1.0 eq) in 120 mL DCM was cooled to −5° C., and tetrabutyl-ammonium nitrate (5.17 g, 17 mmol, 1.36 eq) in DCM (30 mL) was added drop wise below 0° C., then TFAA (5.17 g, 20 mmol, 1.6 eq) was added all at once. After addition, the reaction mixture was stirred at −5° C. for 1 hr and then warmed up to 25° C. and stirred for 15 hrs. The solvent was concentrated, and ether (200 mL) was added to the residue, stirred and filtered. Collected filter-cake and saturated sodium bicarbonate solution (100 mL) was added. The mixture was extracted twice with ethyl acetate, then the combined organic layers was dried over anhydrous sodium sulfate and concentrated to give compound A1-12 as a yellow powder (1.37 g, yield 61.4%). MS-ESI:$[M+1]^+$: 181

Step 11. A mixture of compound A1-12 (1.37 g, 7.61 mmol, 1.0 eq) and propionic acid (50 mL) was heated to 110° C., then fuming nitric acid (0.65 mL) was added dropwise at 110° C. to 120° C. After stirring for 30 mins at 125° C. and cooled to room temperature, ether (100 mL) was added, and the solid was filtered, washed with ether and dried under vacuum to give compound A1-13 as yellow a powder (1.2 g, yield 87.6%). MS-ESI:$[M+1]^+$: 181.

$^1$H NMR (300 MHz, $d_6$-DMSO): 13.149 (s, 1H), 9.024 (s, 1H), 8.234 (d, 1H), 6.966 (d, 1H).

Step 12. To a solution of compound A1-13 (1.2 g, 6.67 mmol, 1.0 eq) in 1,2-dichloroethane (50 mL), was added phosphorus oxychloride (15 mL) below 20° C., then stirred for 2 hrs at 95° C. in nitrogen atmosphere, cooled to 25° C. and concentrated. The residue was slowly added saturated sodium bicarbonate solution to pH 7-8 below 20° C., and the mixture was extracted twice with MTBE. The combined organic layers was washed with brine, dried over anhydrous sodium sulfate, concentrated to give compound A1-14 as a light-yellow powder (0.8 g, yield 60.4%), $^1$H NMR (300 MHz, $CDCl_3$): 9.250 (s, 1H), 8.189 (d, 1H), 7.191 (d, 1H).

Step 13. To a solution of A1-14 (280 mg, 1.41 mmol, 1.0 eq) in n-butanol (20 mL) was added compound A1-4 (290 mg, 2.34 mmol, 1.66 eq) and DIPEA (403 mg, 3.12 mmol, 2.21 eq). The reaction mixture was stirred for 1 hr at 135° C., concentrated and purified by silica gel column chromatography to give A1-15 as a yellow powder (320 mg, yield 79.4%). MS-ESI:$[M+1]^+$: 287.1.

$^1$H NMR (300 MHz, $CDCl_3$): 9.268 (s, 1H), 8.653 (d, 1H), 7.952 (d, 1H), 7.034 (d, 1H), 4.423-4.511 (m, 1H), 2.629-2.723 (m, 1H), 2.241-2.355 (m, 4H), 1.864-1.902 (m, 2H), 1.539-1.578 (m, 2H).

Step 14. To a solution of A1-15 (320 mg, 1.12 mmol, 1.0 eq) in methanol (15 mL), was added 10% Pd/C (0.3 g, 50% wet). Hydrogenation was carried out under atmospheric pressure at room temperature until hydrogen uptake ceased. The catalyst was filtered and washed by methanol. The filtrates was concentrated under vacuum, and A1-16 was obtained as a yellow oil (286 mg, yield 100%). MS-ESI: $[M+1]^+$: 257.1

Step 15. A solution of (R)-(+)-Lactamide (259 mg, 2.8 mmol, 5.0 eq) and Et3O—BF4 (543 mg, 2.8 mmol, 5.0 eq) in THF (10 mL) was stirred 30 mins at room temperature in nitrogen atmosphere. Then the above solution was added to the mixture of A1-16 (143 mg, 0.56 mmol, 1.0 eq) in ethanol (10 mL). After stirring for 2 hrs at 85° C., the mixture was concentrated, added water and extracted four times with ethyl acetate. The organic phase was discarded and the aqueous phase was treated with saturated sodium bicarbonate solution (100 mL) to pH 8, extracted twice with ethyl acetate. The second organic phases was dried over anhydrous sodium sulfate, concentrated to give the title compound as a light-yellow powder (80 mg, yield 46%). MS-ESI: $[M+1]^+$: 311.4

$^1$H NMR (300 MHz, $CDCl_3$): 9.005 (s, 1H), 7.949 (s, 1H), 7.256 (s, 1H), 5.227-5.290 (m, 1H), 4.766-4.843 (m, 1H), 2.783-2.864 (m, 1H), 2.438-2.527 (m, 4H), 2.068-2.192 (m, 2H), 1.913-2.003 (m, 2H), 1.767-1.846 (d, 3H).

Example 2: Synthesis of trans-4-[2-(Hydroxymethyl)furo[3,2-b]imidazo[4,5-d]pyridin-1-yl]cyclohexanecarbonitrile (2)

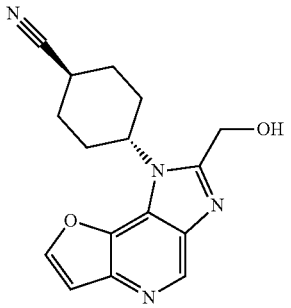

Scheme 2

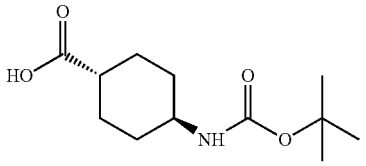

A1-1

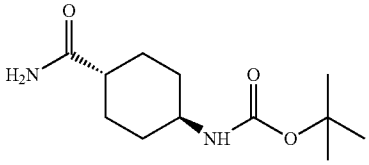

A1-2

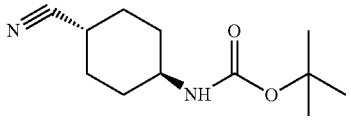

A1-3

-continued

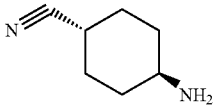

A1-4

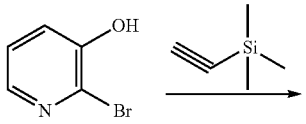

A1-5

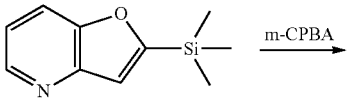

A1-6

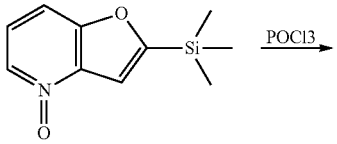

A1-7

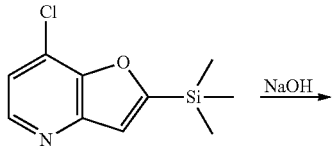

A1-8

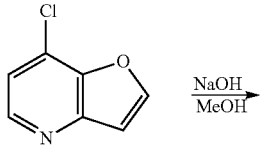

A1-9

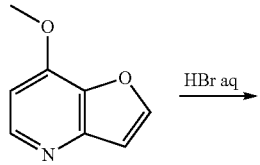

A1-10

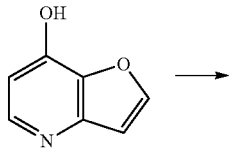

A1-11

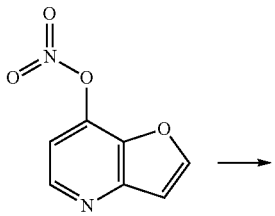

A1-12

-continued
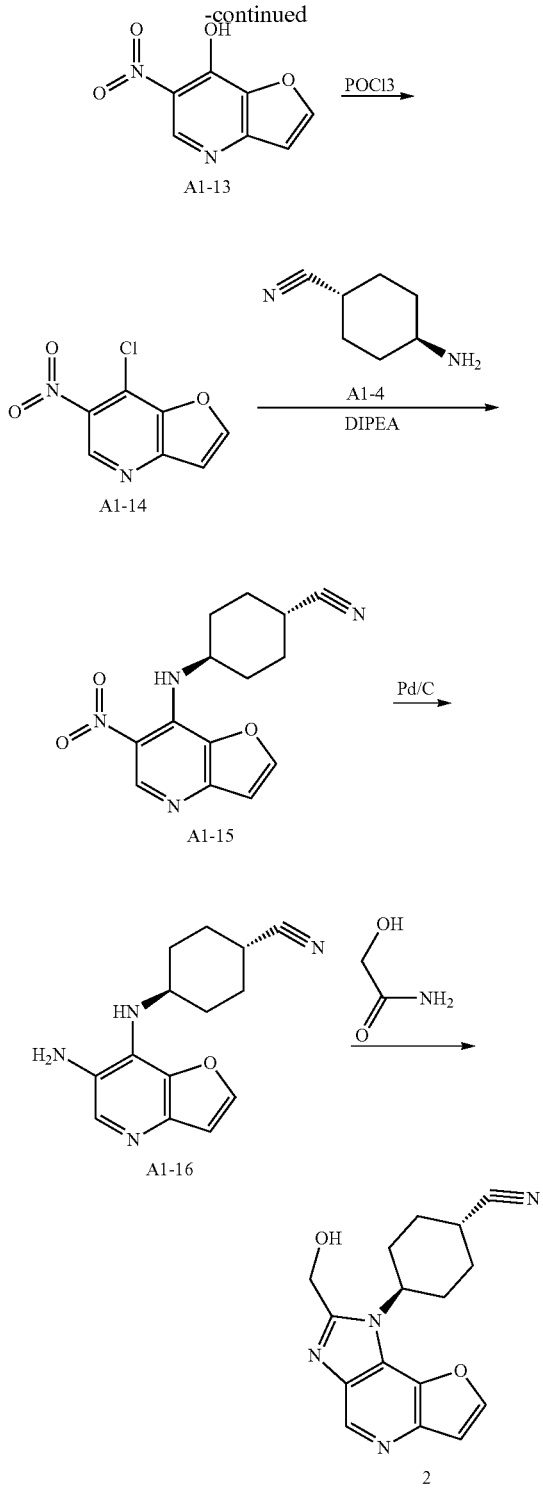
Example 2 was made using the same procedure as Example 1 except that (R)-(+)-Lactamide is replaced by 2-hydroxyacetamide in step 15): 40 mg of title compound as a light-yellow powder, MS-ESI: $[M+1]^+$: 297.4
$^1$H NMR (300 MHz, $CDCl_3$): 9.048 (s, 1H), 7.965 (s, 1H), 7.286 (s, 1H), 5.049 (s, 2H), 4.702-4.813 (m, 1H), 2.753-2.873 (m, 1H), 2.376-2.527 (m, 4H), 2.087-2.226 (m, 2H), 1.872-2.053 (m, 2H).
Example 3: Synthesis of 2-[trans-4-[2-[(R)-1-Hydroxyethyl]furo[3,2-b]imidazo[4,5-d]pyridin-1-yl] cyclohexyl] acetonitrile (3)
3
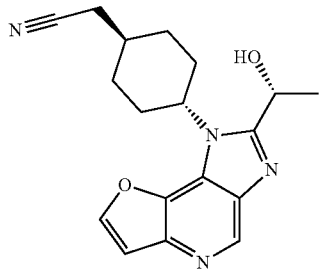
Scheme 3
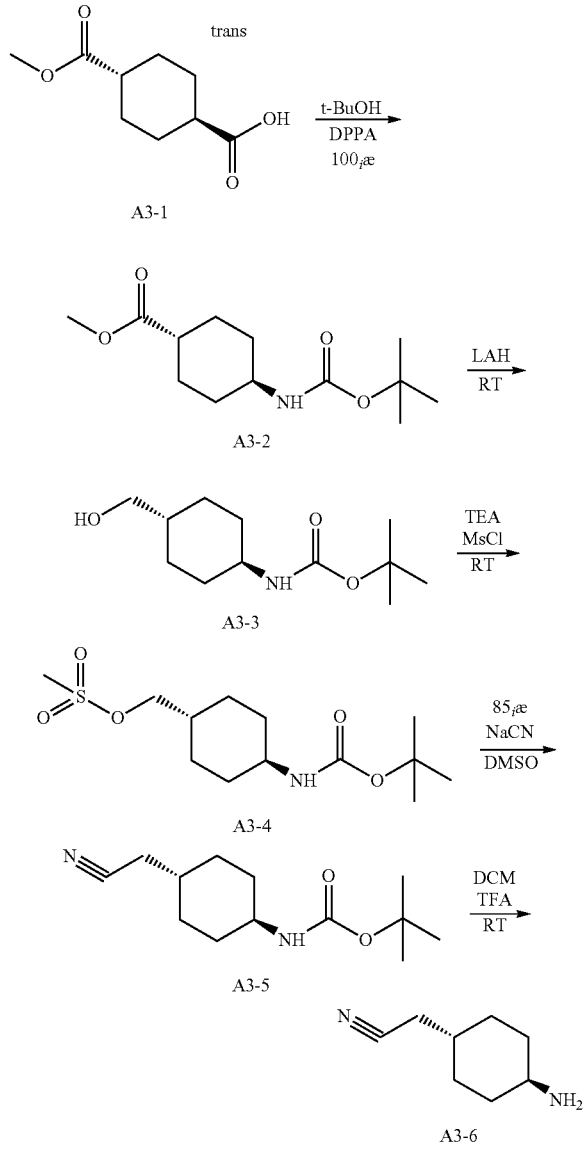

-continued

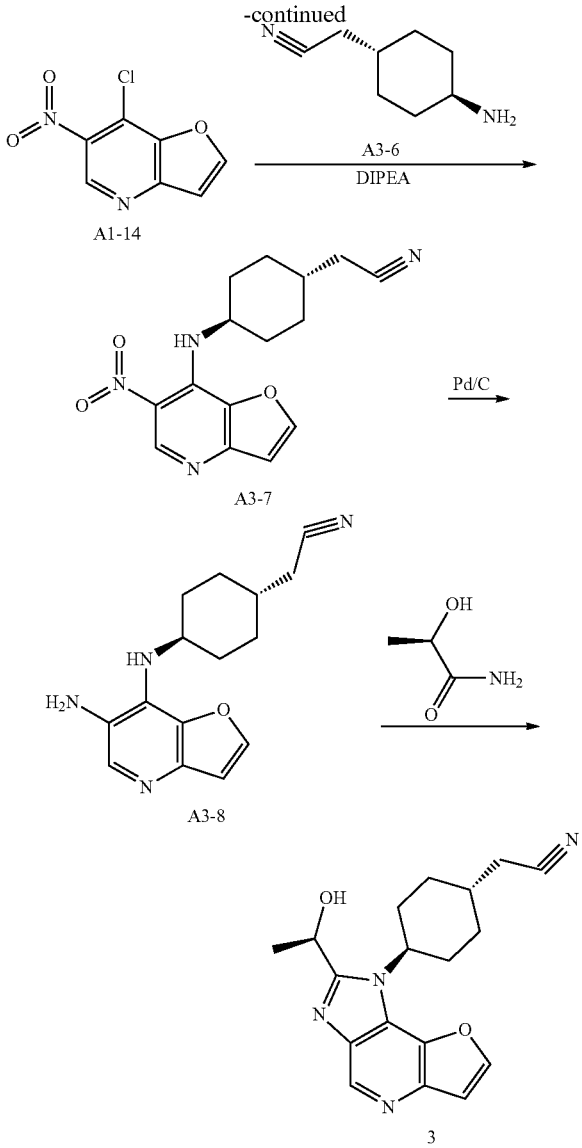

Step 1. In nitrogen atmosphere, to a solution of trans-1,4-cyclohexane-dicarboxylic acid monomethyl ester (A3-1) (100 g, 0.538 mol, 1.0 eq) and triethylamine (57.4 g, 0.568 mol, 1.055 eq) in t-butyl alcohol (1000 mL) was added dropwise diphenylphosphoryl azide (155 g, 0.563 mol, 1.047 eq) at room temperature. The mixture was refluxed over 16 hrs. Upon completion by TLC, the mixture was then cooled and concentrated. Water (1000 mL) was added, and the mixture was extracted three times with MTBE. Then the organic layer was washed with saturated sodium bicarbonate solution and brine, dried over anhydrous sodium sulfate, concentrated and purified by silica gel column chromatography to give compound A3-2 as an off-white powder (53 g, yield 39.2%). MS-ESI:$[M+1]^+$: 257.1

Step 2. A suspension of $LiAlH_4$ (9.0 g, 0.236 mol, 1.12 eq) in THF (500 mL) was cooled to 0° C. in ice-bath, and then added a solution of compound A3-2 (54.3 g, 0.211 mol, 1.0 eq) in THF (200 mL) while keeping the temperature below 10° C. The reaction mixture was stirred overnight at room temperature, and then quenched with sodium sulfate decahydrate (27 g) at 15° C. to 25° C., filtered and the filtrate was concentrated to give compound A3-3 as a white powder (43 g, yield 89%).

MS-ESI:$[M+1]^+$: 229.1

Step 3. A mixture of compound A3-3 (11.5 g, 0.05 mol, 1.0 eq) and triethylamine (7.6 g, 0.075 mol, 1.5 eq) in DCM (200 mL), was added methylsufonyl chloride (6.9 g, 0.06 mol, 1.2 eq) dropwise below 10° C. After stirring for 2 hrs at room temperature, water (300 mL) was added. The mixture was extracted twice with ethyl acetate. The combined extracts was washed with brine, dried over anhydrous sodium sulfate, concentrated to give compound A3-4 as yellow liquid (16.0 g, yield 100%). MS-ESI:$[M+1]^+$: 307.1

Step 4. To a solution of compound A3-4 (16.0 g, 0.05 mol, 1.0 eq) in DMSO (150 mL) was added sodium cyanide (7.0 g, 0.143 mol, 2.86 eq) in portions below 20° C. After stirring for 5 hrs at 85° C., the mixture was cooled to room temperature, ice-water (500 mL) was added. The mixture was extracted twice with MTBE. The combined extracts was washed three times with brine, dried over anhydrous sodium sulfate, concentrated and purified by silica gel column chromatography to give compound A3-5 as white powder (9.3 g, yield 78%). MS-ESI:$[M+1]^+$: 238.1.

$^1H$ NMR (300 MHz, $CDCl_3$): 4.408 (m, 1H), 3.405 (m, 1H), 2.263-2.285 (d, 2H), 2.064-2.096 (m, 2H), 1.457 (s, 9H), 1.122-1.281 (m, 4H).

Step 5. To a solution of compound A3-5 (1.1 g, 4.6 mmol, 1.0 eq) in DCM (10 mL) was added TFA (6 g). The reaction mixture was stirred for 2 hrs at room temperature, then concentrated under vacuum. Ice-water (15 mL) was added and the solution was treated with aqueous sodium hydroxide solution (4 mol/L) to pH 10. Then the aqueous phase was extracted five times with DCM/methanol (10/1). The combined extracts was dried over anhydrous sodium sulfate, concentrated to give compound A3-6 as a yellow oil (0.55 g, yield 87.7%). MS-ESI:$[M+1]^+$: 138.1.

Step 6 to step 8 are the same as step 13 to step 15 in Example 1 except that the amine A1-4 is replaced by A3-6 to make the title compound: 70 mg of light-yellow powder (Yield: 0.565%). MS-ESI: $[M+1]^+$: 325.5

$^1H$ NMR (300 MHz, $CDCl_3$): 9.003 (s, 1H), 7.965 (s, 1H), 7.270 (s, 1H), 5.255-5.298 (m, 1H), 4.713-4.795 (m, 1H), 2.439-2.611 (m, 4H), 2.068-2.512 (m, 5H), 1.808-1.829 (d, 3H), 1.452-1.576 (d, 2H).

Example 4: Synthesis of 2-[(2R,5S)-5-[2-[(R)-1-Hydroxyethyl]furo[3,2-b]imidazo[4,5-d]pyridin-1-yl]tetrahydropyran-2-yl] acetonitrile (4)

4

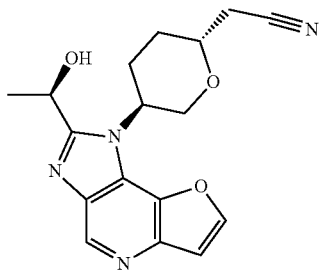

Scheme 4

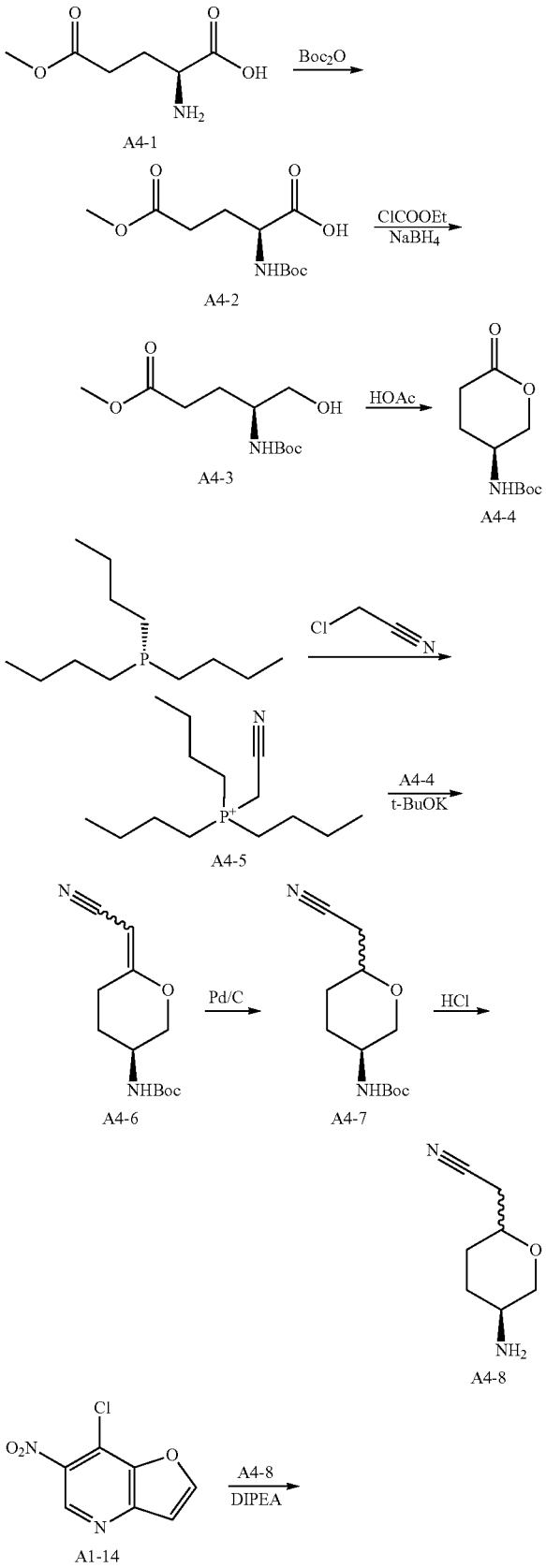

-continued

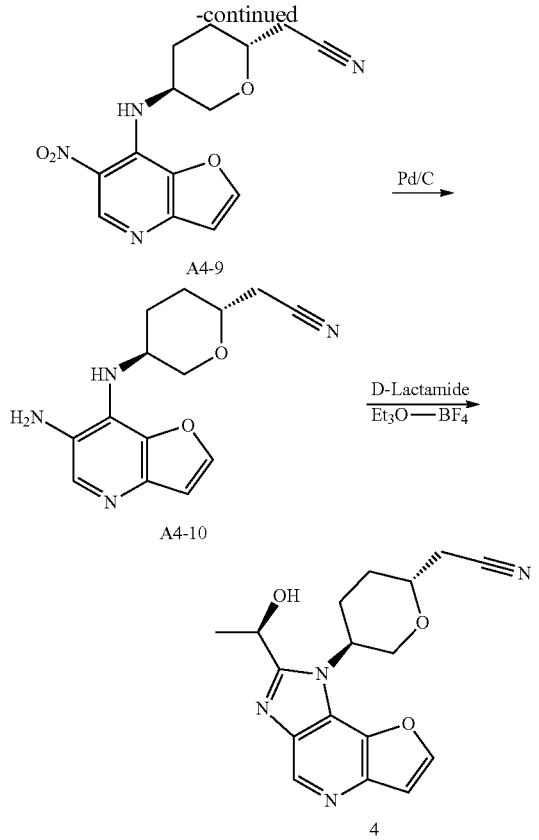

Step 1. In a round bottom flask, triethylamine (188 g, 1.86 mol, 1.0 eq) was added dropwise to a stirred solution of di-tert-butyl dicarbonate (162 g, 0.744 mol, 1.2 eq) and compound A4-1 (100 g, 0.62 mol, 1.0 eq) in water (500 mL) and 1,4-dioxane (500 mL). After stirring for 18 hrs at room temperature, the solution was extracted with MTBE (500 mL*2) and the aqueous phase was cooled on ice and carefully acidified to pH 3 by slow addition of 10% citric acid solution. The urethane was then extracted twice with ethyl acetate, and the combined extracts was washed with brine, dried over anhydrous sodium sulfate, and concentrated to give compound A4-2 as clear viscous oil (180 g, yield 100%). MS-ESI:$[M+1]^+$: 262.1

Step 2. A solution of compound A4-2 (40 g, 0.153 mmol, 1.0 eq) in THF (600 mL) was treated with 4-methylmorpholine (17 g, 0.168, 1.1 eq) at room temperature. The resulting mixture was cooled to 0° C. before being treated with isobutyl chloroformate (22.7 g, 0.166 mmol, 1.08 eq) dropwise. The resulting reaction mixture was stirred at 0° C. for an addition 20 mins before being filtered and washed with THF. Then the clear filtrate solution was cooed to 0° C., and treated with a solution of $NaBH_4$ (11.2 g, 0.295 mol, 1.93 eq) in water (100 mL). The resulting mixture was stirred overnight at room temperature, and then quenched with an aqueous HCl solution (1.0 mol/L,200 mL) dropwise, The mixture was extracted with ethyl acetate, and the combined extracts was washed with brine, dried over anhydrous sodium sulfate, concentrated to give compound A4-3 as a yellow oil (25 g, yield 66%). MS-ESI:$[M+1]^+$: 248.1

Step 3. A solution of compound of A4-3 (25 g, 0.1 mol, 1.0 eq) in toluene (300 mL) and acetic acid (150 mL) was heated to reflux for 5 hrs and then cooled, concentrated under vacuum. The residual was added saturated sodium bicarbonate solution to pH 7-8 in ice-bath. Then the mixture was extracted three times with ethyl acetate, and the combined extracts was washed with brine, dried over anhydrous sodium sulfate, concentrated and recrystallized by ethyl acetate and PE to give compound A4-4 as a white powder (8.0 g, yield 37.2%). GC-MS: 215

Step 4. A solution of tributyl phosphine (72.9 g, 0.36 mol, 1.0 eq) in nitromethane (500 mL), was added dropwise chloroacetonitrile (27.2 g, 0.36 mol, 1.0 eq) in nitrogen atmosphere. The resulting reaction mixture was stirred for 16 hrs at room temperature, then concentrated. The residual oil solidified when a small amount of ethyl acetate was added. The solid was recrystallized by ethyl acetate and DCM to afford compound A4-5 as a white powder (95 g, yield 95%).

Step 5. To a solution of dry compound A4-5 (8.3 g, 30 mmol, 3.0 eq) in N,N-dimethylacetamide (30 mL) in nitrogen atmosphere, was added solid Potassium tert-butoxide (3.1 g, 28 mmol, 2.8 eq) in portions at 0° C. The resulting mixture was gradually warmed to 30° C. and stirred for 2 hrs. The resulting ylide solution was then treated with compound A4-4 (2.15 g, 10 mmol, 1.0 eq), and stirred overnight at 70° C. After cooled to room temperature, the resulting slurry was poured into the mixture of ice-water (100 mL) and saturated sodium bicarbonate solution (100 mL). The mixture was extracted twice with ethyl acetate, and the combined extracts was washed three times with brine, dried over anhydrous sodium sulfate, concentrated to give compound A4-6 as yellow oil without purification (7.5 g, yield 100%). MS-ESI:$[M+1]^+$: 239.1

Step 6. To a solution of compound A4-6 (7.5 g, 10 mmol, 1.0 eq) in methanol (200 mL), was added 10% Pd/C (0.5 g,50% wet). Hydrogenation was carried out under atmospheric pressure at room temperature until hydrogen uptake ceased. The catalyst was filtered and washed by methanol. The filtrates was concentrated under vacuum, and purified by silica gel column chromatography to give compound A4-7 as off-white powder (1.6 g, yield 66.7%). MS-ESI: $[M+1]^+$: 241.1

Step 7. To a solution of compound A4-7 (1.6 g, 6.67 mmol, 1.0 eq) in DCM (20 mL), was added TFA (10 g, 88.5 mmol, 13.2 eq). The reaction mixture was stirred for 2 hrs at room temperature until TLC showed the reaction was complete, then concentrated under vacuum. Water (20 mL) was added and the solution was treated with aqueous sodium hydroxide solution (4 mol/L) to pH 10. Then the aqueous phase was extracted six times with DCM/methanol (10/1). The combined extracts was dried over anhydrous sodium sulfate, concentrated to give compound A4-8 as light-brown oil (950 mg, yield 100%). MS-ESI:$[M+1]^+$: 141.1

Step 8. To a solution of compound A1-14 (prepared as step 4 to 12 in example 1) (600 mg, 3.0 mmol, 1.0 eq) in n-butanol (15 mL), was added compound A4-8 (950 mg, 6.7 mmol, 2.26 eq) and DIPEA (1.36 g, 10.5 mmol, 3.5 eq). The reaction mixture was stirred for 1 hr at 135° C., concentrated and purified by silica gel column chromatography to give compound A4-9 (2R,5S) as light-yellow powder (254 mg, yield 28.0%).MS-ESI: $[M+1]^+$: 303.1.

$^1$H NMR (300 MHz, $d_6$-DMSO): 9.063 (s, 1H), 8.503 (d, 1H), 9.326 (d, 1H), 7.176 (d, 1H), 4.431-4.513 (m, 1H), 4.128-4.156 (m, 1H), 3.633-3.659 (m, 1H), 3.448-3.518 (m, 1H), 2.775-2.841 (m, 2H), 2.205-2.312 (m, 1H), 1.829-1.859 (m, 2H), 1.501-1.521 (m, 1H).

Step 9. To a solution of compound A4-9 (254 g, 0.84 mmol, 1.0 eq) in methanol (20 mL), was added 10% Pd/C (0.15 g,50% wet). Hydrogenation was carried out under atmospheric pressure at room temperature until hydrogen uptake ceased. The catalyst was filtered and washed by methanol. The filtrates was concentrated under vacuum, and compound A4-10 was obtained as yellow oil (230 mg, yield 100%). MS-ESI:$[M+1]^+$: 273.1

Step 10. A solution of D-Lactamide (388 mg, 4.2 mmol, 5.0 eq) and Et3O—$BF_4$ (1.3 g, 6.72 mmol, 8.0 eq) in THF (10 mL) was stirred for 30 mins at room temperature in nitrogen atmosphere. Then the above solution was added to the mixture of compound A4-10 (230 mg, 0.84 mmol, 1.0 eq) in ethanol (10 mL). After stirring for 3 hrs at 85° C. until HPLC showed the reaction was complete, the mixture was concentrated, added water and extracted four times with ethyl acetate. The organic phases was discarded and the aqueous phase was treated with saturated sodium bicarbonate solution to pH 8, extracted twice with ethyl acetate. The second organic phases was dried over anhydrous sodium sulfate, concentrated and purified by silica gel column chromatography to give the title compound as light-yellow powder (120 mg, yield 43.8%). MS-ESI: $[M+1]^+$: 327.6, $^1$H NMR (300 MHz, $CDCl_3$): 9.039 (s, 1H), 7.939 (d, 1H), 7.196 (d, 1H), 5.235-5.336 (m, 1H), 4.806-4.973 (m, 1H), 4.403-4.483 (t, 1H), 4.096-6.116 (m, 2H), 2.700-2.807 (m, 4H), 2.105-2.312 (m, 2H), 1.830-1.852 (d, 3H).

Example 5: Synthesis of 3-[2-[(R)-1-Hydroxyethyl]-1H-furo[3,2-b]imidazo[4,5-d] pyridin-1-yl]-N-(2,2,2-trifluoroethyl)pyrrolidine-1-carboxamide (5)

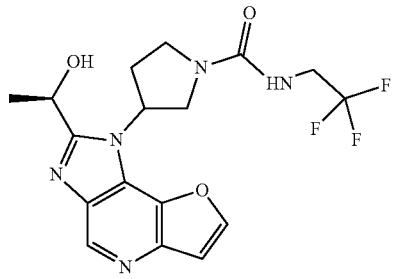

Scheme 5

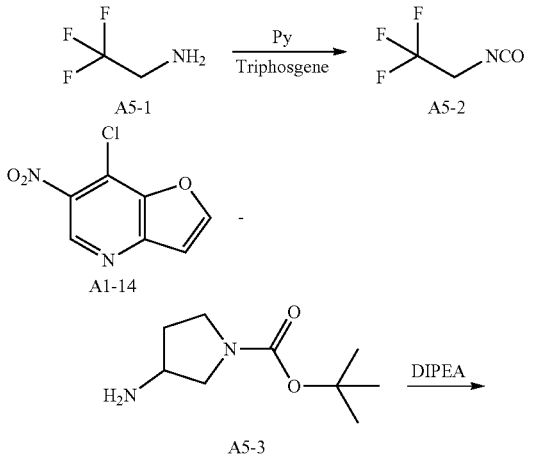

-continued

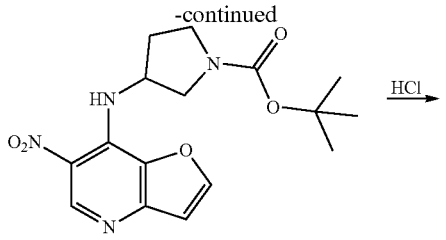

A5-4

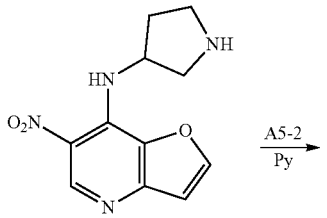

A5-5

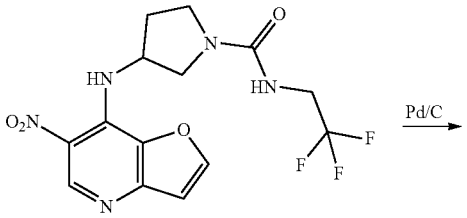

A5-6

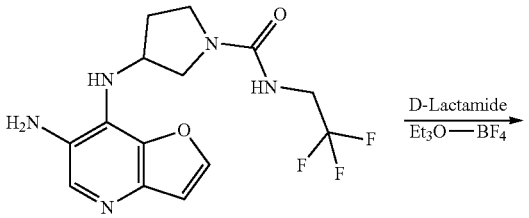

A5-7

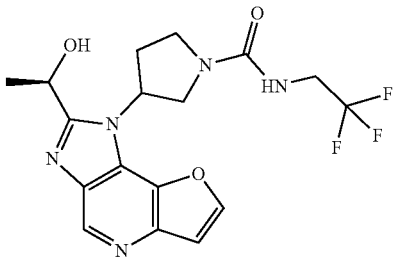

5

Step 1. To a solution of compound A1-14 (prepared as step 4 to 12 in example 1) (820 mg, 4.13 mmol, 1.0 eq) in n-butanol (15 mL), was added compound A5-3 (1.0 g, 5.37 mmol, 1.3 eq) and DIPEA (1.6 g, 12.4 mmol, 3.0 eq). The reaction mixture was stirred for 1 hr at 135° C., concentrated and purified by silica gel column chromatography to give compound A5-4 as yellow powder (1.32 g, yield 91.8%). MS-ESI:$[M+1]^+$: 349.1

Step 2. To a solution of compound A5-4 (1.32 g, 3.8 mmol, 1.0 eq) in DCM (15 mL), was added a solution of HCl in ethanol (30% w/w) (15 mL). The reaction mixture was stirred for 2 hrs at room temperature until TLC showed the reaction was complete, then concentrated under vacuum. Ice-water (20 mL) was added and the solution was treated with aqueous sodium hydroxide solution (4 mol/L) to pH 10. Then the aqueous phase was extracted three times with DCM. The combined extracts was dried over anhydrous sodium sulfate, concentrated to give compound A5-5 as yellow powder (950 mg, yield 100%). MS-ESI:$[M+1]^+$: 249.1

Step 3. A mixture of 2,2,2-trifluoroethylamine (A5-1) (1.21 g, 12.2 mmol, 1.0 eq) and pyridine (2.4 g, 30.5 mmol, 2.5 eq) in DCM (50 mL) was cooled to 0° C., and treated with triphosgene (1.34 g, 4.52 mmol, 0.37 eq) in DCM (50 mL) dropwise below 5° C. After addition, the reaction mixture was stirred at 35° C. for 1 hr and then 25° C. for 2 hrs. The isocyanate (A5-2) solution was used for next step without purification.

Step 4. A mixture of compound A5-5 (0.95 g, 3.8 mmol, 1.0 eq) and pyridine (0.45 g, 5.7 mmol, 1.5 eq) in DCM (60 mL) was cooled to 10° C., and treated with the isocyanate (A5-2) solution (12.2 mmol, 3.2 eq) dropwise. The reaction mixture was heated to reflux for 3 h, and then cooled. Saturated sodium bicarbonate solution (200 mL) was added, the mixture was extracted twice with DCM. The combined extracts was washed brine, dried over anhydrous sodium sulfate, concentrated and purified by silica gel column chromatography to give compound A5-6 as yellow powder (850 mg, yield 60%). MS-ESI:$[M+1]^+$: 374.3

$^1$H NMR (300 MHz, $d_6$-DMSO): 9.282 (s, 1H), 8.718 (d, 1H), 7.962 (d, 1H), 7.024 (d, 1H), 5.165-5.186 (m, 1H), 4.642 (m, 1H), 3.926-4.008 (m, 3H), 3.517-3.675 (m, 3H), 2.502-2.568 (m, 1H), 2.206-2.267 (m, 2H).

Step 5. To a solution of compound A5-6 (850 mg, 2.28 mmol, 1.0 eq) in methanol (80 mL), was added 10% Pd/C (0.45 g, 50% wet). Hydrogenation was carried out under atmospheric pressure at room temperature until hydrogen uptake ceased. The catalyst was filtered and washed by methanol. The filtrate was concentrated under vacuum, and compound A5-7 was obtained as brown oil (800 mg, yield 100%). MS-ESI:$[M+1]^+$: 344.3

Step 6. A solution of D-Lactamide (1.27 g,13.68 mmol,6.0 eq) and Et3O—BF4 (3.53 g, 18.24 mmol, 8.0 eq) in THF (20 mL) was stirred 30 min at room temperature in nitrogen atmosphere. Then the above solution was added to the mixture of compound A5-7 (800 mg, 2.28 mmol, 1.0 eq) in ethanol (20 mL). After stirring for 5 hrs at 85° C. until HPLC showed the reaction was complete, the mixture was concentrated, added HCl (1 mol/L, 30 mL) and extracted four times with ethyl acetate. The organic phases was discarded and the aqueous phase was treated with saturated sodium bicarbonate solution to pH 8, extracted three times with ethyl acetate. The second organic phase was dried over anhydrous sodium sulfate, concentrated and purified by silica gel column chromatography to give the title compound as light-yellow powder (530 mg, yield 58.5%). MS-ESI:[M−1]: 396.5.

$^1$H NMR (300 MHz, $d_6$-DMSO): 8.931 (s, 1H), 8.338 (d, 1H), 7.276 (d, 1H), 7.007 (m, 1H), 5.889-5.910 (m, 1H), 5.661-5.683 (m, 1H), 5.251-5.273 (m, 2H), 3.652-3.970 (m, 5H), 3.435-3.505 (m, 1H), 2.455-2.712 (m, 2H), 1.672 (d, 3H).

Example 6: Synthesis of (R)-4-[2-(1-Hydroxyethyl)-1H-furo[3,2-b]imidazo[4,5-d]pyridin-1-yl]-N-(2,2,2-trifluoroethyl)piperidine-1-carboxamide (6)

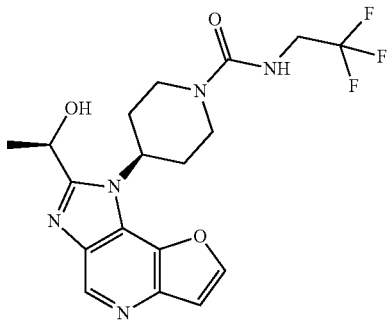

Scheme 6

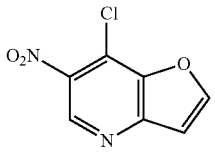

A1-14

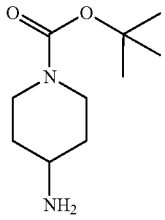

A6-1

DIPEA

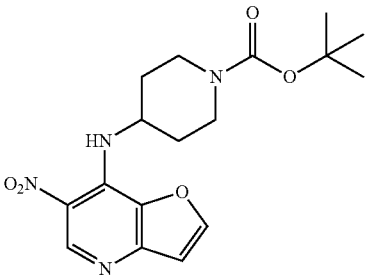

A6-2

HCl

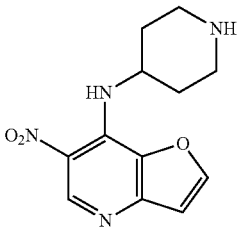

A6-3

A5-2
Py

-continued

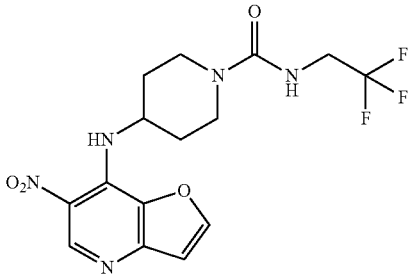

A6-4

Pd/C

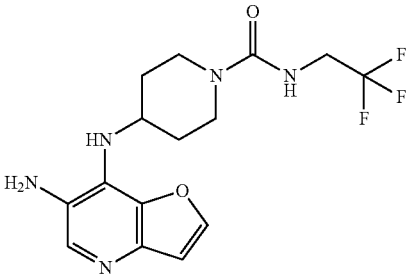

A6-5

D-Lactamide
$Et_3O—BF_4$

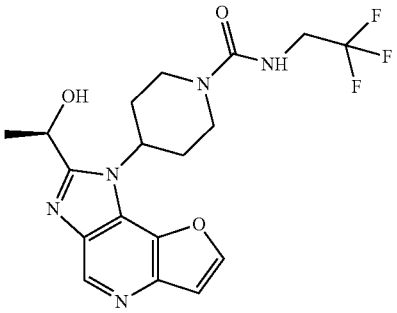

6

The procedures are similar to those in Example 5 to produce the title compound as an off-white powder (21 mg, Yield:6.7%), MS-ESI:$[M-1]^-$:410.6.

$^1$H NMR (300 MHz, CD3OD): 8.862 (s, 1H), 8.046 (d, 1H), 7.150 (d, 1H), 5.152-5.383 (m, 2H), 4.325-4.386 (m, 2H), 3.990-4.022 (m, 2H), 3.110-3.192 (m, 2H), 2.423-2.653 (m, 2H), 1.984-2.117 (m, 2H), 1.793-1.915 (d, 3H).

Example 7: Synthesis of 2-[(2R,5S)-5-[2-(Hydroxymethyl)furo[3,2-b]imidazo[4,5-d]pyridin-1-yl] tetrahydropyran-2-yl] acetonitrile (7)

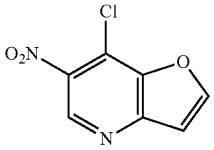

A1-14

+

-continued

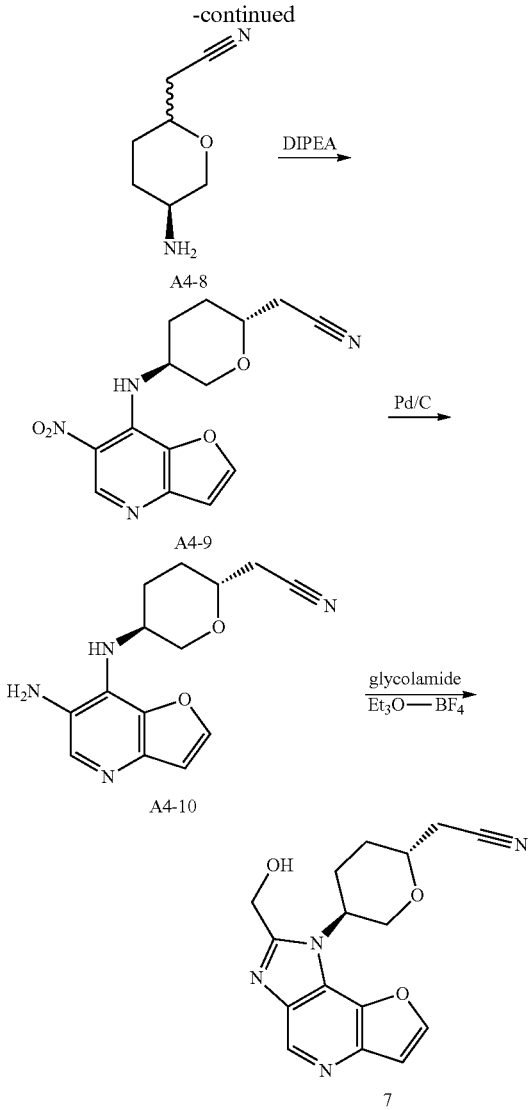

Step 1. In nitrogen atmosphere, to a solution of compound A1-14 (500 mg, 2.0 mmol, 1.0 eq) in butyl alcohol (8 mL), were added compound A4-8 (350 mg, 2.5 mmol, 1.0 eq) and DIPEA (403 mg, 8.25 mmol, 3.3 eq). The reaction mixture was stirred 2 hrs at 135° C., then concentrated and purified by silica gel column chromatography to give compound A4-9 as yellow solid (194 mg, yield 25.6%). MS-ESI:[M+1]$^+$: 302.3

Step 2. To a solution of compound A4-9 (97 mg, 1.0 mmol) in methanol (15 mL), was added 10% Pd/C (50 mg, 50% wet). Hydrogenation was carried out under atmospheric pressure at room temperature until hydrogen uptake ceased. The catalyst was filtered and washed by methanol. The filtrate was concentrated to give compound A4-10 as yellow oil (535 mg, yield: 100%). MS-ESI: [M+1]$^+$: 272.5

Step 3. A solution of glycolamide (126 mg, 1.6 mmol, 5.0 eq) and Et3O—BF4 (310 mg, 1.6 mmol, 5.0 eq) in THF (10 mL) was stirred 30 mins at room temperature in nitrogen atmosphere. Then the above solution was added to the mixture of compound A4-10 (88 mg, 0.32 mmol, 1.0 eq) in ethanol (10 mL). After stirring 12 hrs at 85° C., the mixture was concentrated, added water and extracted three times with ethyl acetate. The organic phases were discarded and the aqueous phase was treated with saturated sodium bicarbonate solution (100 mL) to pH: 8, then the mixture was extracted twice with ethyl acetate. The second organic phase was dried over anhydrous sodium sulfate, concentrated and purified by silica gel column chromatography to give the title compound as an off-white powder (70 mg, yield: 70%). MS-ESI: [M+1]+: 313.5

1H NMR (300 MHz, $CDCl_3$): 9.00 (s, 1H), 7.95 (d, 1H), 7.26 (d, 1H), 5.27-5.29 (m, 1H), 4.76-4.84 (m, 1H), 2.78-2.86 (m, 1H), 2.43-2.52 (m, 4H), 2.06-2.19 (m, 2H), 1.91-2.00 (m, 2H), 1.76-1.84 (d, 3H).

Example 8: Synthesis of 2-[(2S,5S)-5-[2-(Hydroxymethyl)furo[3,2-b]imidazo[4,5-d]pyridin-1-yl] tetrahydropyran-2-yl] acetonitrile (8)

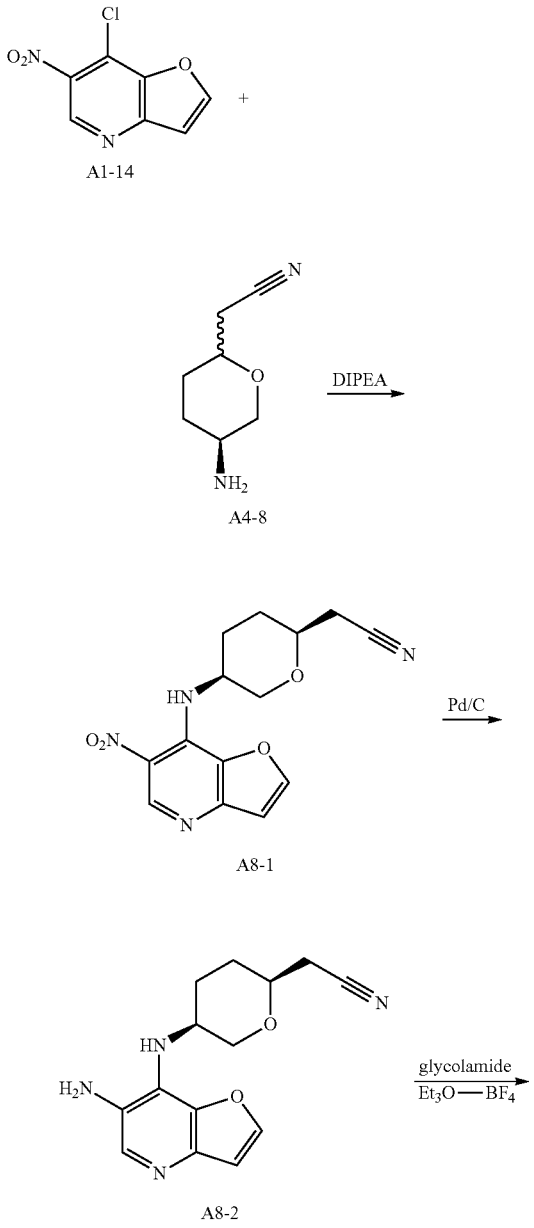

-continued

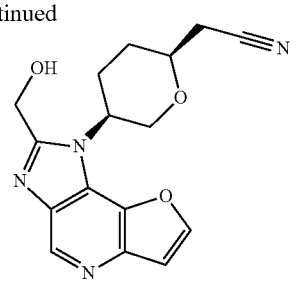

8

Step 1. In nitrogen atmosphere, to a solution of compound A1-14 (500 mg, 2.0 mmol, 1.0 eq) in butyl alcohol (8 mL), were added compound A4-8 (350 mg, 2.5 mmol, 1.0 eq) and DIPEA (403 mg, 8.25 mmol, 3.3 eq). The reaction mixture was stirred 2 hrs at 135° C., then concentrated and purified by silica gel column chromatography to give compound A8-1 as yellow solid (67 mg, yield 8.84%).

MS-ESI:$[M+1]^+$: 302.3

Step 2. To a solution of compound A8-1 (67 mg, 1.0 mmol) in methanol (10 mL), was added 10% Pd/C (30 mg, 50% wet). Hydrogenation was carried out under atmospheric pressure at room temperature until hydrogen uptake ceased. The catalyst was filtered and washed by methanol. The filtrate was concentrated to give compound A8-2 as yellow oil (60 mg, yield: 100%).

MS-ESI: $[M+1]^+$: 272.5

Step 3. A solution of glycolamide (105 mg, 1.33 mmol, 6.0 eq) and $Et_3O—BF_4$ (258 mg, 1.33 mmol, 6.0 eq) in THF (10 mL) was stirred 30 mins at room temperature in nitrogen atmosphere. Then the above solution was added to the mixture of compound A8-2 (60 mg, 0.221 mmol, 1.0 eq) in ethanol (10 mL). After stirring 12 hrs at 85° C., the mixture was concentrated, added water and extracted three times with ethyl acetate. The organic phases was discarded and the aqueous phase was treated with saturated sodium bicarbonate solution (100 mL) to pH: 8, then the mixture was extracted twice with ethyl acetate. The second organic phases was dried over anhydrous sodium sulfate, concentrated and purified by silica gel column chromatography to give the title compound as an off-white powder (21 mg, yield: 30.5%).

MS-ESI: $[M+1]^+$: 313.5

$^1H$ NMR (300 MHz, $CD_3OD$): 8.85 (s, 1H), 8.29 (d, 1H), 7.18 (d, 1H), 4.98 (d, 3H), 4.35-4.42 (m, 2H), 3.95-3.99 (m, 1H), 3.48-3.65 (m, 1H), 3.04-3.11 (m, 1H), 2.67-2.76 (m, 1H), 1.97-2.31 (m, 3H).

Example 9: Synthesis of 2-[(2R,5S)-5-[2-Ethylfuro[3,2-b]imidazo[4,5-d] pyridin-1-yl]tetrahydropyran-2-yl] acetonitrile (9)

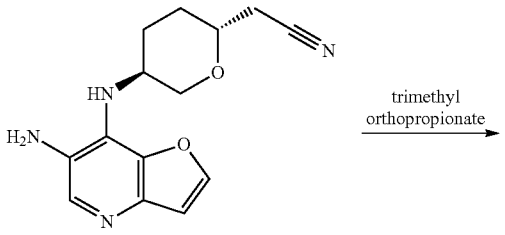

A4-10

-continued

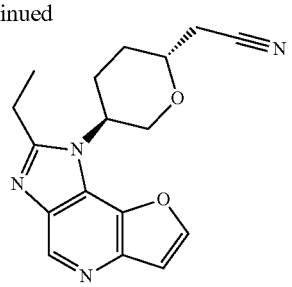

9

In nitrogen atmosphere, a solution of compound A4-10 (1.1 g, 4.04 mmol, 1.0 eq) and trimethyl ortho-propionate (2.2 mL) in 1,2-dichloroethane (50 mL) was heated to reflux, and then added pyridine hydrochloride (200 mg). The reaction mixture was stirred 2 hrs at 80° C., concentrated, and treated with saturated sodium bicarbonate solution to pH: 8. The mixture was and extracted twice with ethyl acetate. The combined organic phases was dried over anhydrous sodium sulfate, concentrated purified by silica gel column chromatography to give the title compound as a yellow solid (800 mg, yield: 63.8%).

MS-ESI: $[M+1]^+$: 311.0

$^1H$ NMR (300 MHz, $CDCl_3$): 9.01 (s, 1H), 7.91 (d, 1H), 7.17 (d, 1H), 4.54-4.59 (m, 1H), 4.33-4.38 (t, 1H), 4.05-4.09 (m, 2H), 3.01-3.06 (m, 2H), 2.70-2.83 (m, 3H), 2.15-2.19 (m, 2H), 1.85-1.92 (m, 1H), 1.49-1.54 (t, 3H).

Example 10: Synthesis of 2-[(2R,5S)-5-[2-Furo[3,2-b]imidazo[4,5-d] pyridin-1-yl]tetrahydropyran-2-yl] acetonitrile (10)

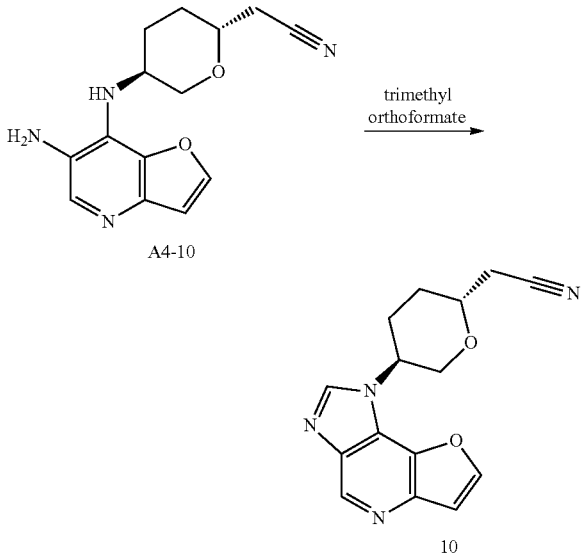

A4-10

10

In nitrogen atmosphere, to a solution of compound A4-10 (136 mg, 0.5 mmol, 1.0 eq) in trimethyl ortho-formate (5.0 mL), was added formic acid (1.0 mL). The reaction mixture was stirred 1 hr at 80° C., concentrated, and treated with saturated sodium bicarbonate solution (100 mL) to pH: 8. The mixture was and extracted twice with ethyl acetate. The combined organic phases was dried over anhydrous sodium sulfate, concentrated purified by silica gel column chromatography to give the title compound as a yellow solid (400 mg, yield: 28.4%).

MS-ESI: $[M+1]^+$: 282.9

$^1$H NMR (300 MHz, $CDCl_3$): 9.10 (s, 1H), 7.94 (s, 1H), 7.92 (d, 1H), 7.19 (d, 1H), 4.76-4.79 (m, 1H), 4.32-4.37 (m, 1H), 3.92-4.03 (m, 2H), 2.71-2.73 (d, 2H), 2.46-2.51 (m, 2H), 2.17-2.21 (m, 1H), 1.89-1.91 (m, 1H).

Example 11: Synthesis of 2-[(2R,5S)-5-[2-Methylfuro [3,2-b]imidazo [4,5-d] pyridin-1-yl]tetrahydropyran-2-yl] acetonitrile (11)

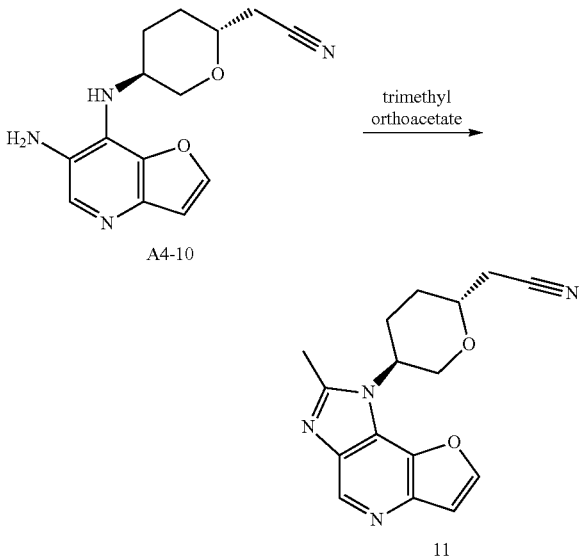

In nitrogen atmosphere, a solution of compound A4-10 (1.0 g, 3.67 mmol, 1.0 eq) and trimethyl ortho-acetate (2.0 mL) in 1,2-dichloroethane (30 mL) was heated to reflux, and then added pyridine hydrochloride (200 mg). The reaction mixture was stirred 2 hrs at 80° C., concentrated, and treated with saturated sodium bicarbonate solution to pH: 8. The mixture was and extracted twice with ethyl acetate. The combined organic phases was dried over anhydrous sodium sulfate, concentrated purified by silica gel column chromatography to give the title compound as yellow solid (500 mg, yield: 46.0%).

MS-ESI: $[M+1]^+$: 296.9

$^1$H NMR (300 MHz, $CDCl_3$): 8.98 (s, 1H), 7.91 (d, 1H), 7.16 (d, 1H), 4.54-4.59 (m, 1H), 4.31-4.38 (t, 1H), 4.02-4.09 (m, 2H), 2.71-2.82 (m, 6H), 2.15-2.22 (m, 2H), 1.85-1.92 (m, 1H).

Biological Test

Example B1: Jak1, 2, 3, Tyk2 Biochemical Assays

Assays were performed by Reaction Biology Corp, Malvern, Pa. The procedure is briefly described below.

Reagent:

Base Reaction buffer; 20 mM Hepes (pH 7.5), 10 mM $MgCl_2$, 1 mM EGTA, 0.02% Brij35, 0.02 mg/ml BSA, 0.1 mM $Na_3VO_4$, 2 mM DTT, 1% DMSO. Required cofactors are added individually to each kinase reaction Reaction Procedure:

1. Prepare indicated substrate in freshly prepared Base Reaction Buffer
2. Deliver any required cofactors to the substrate solution above
3. Deliver indicated kinase into the substrate solution and gently mix
4. Deliver compounds in DMSO into the kinase reaction mixture by Acoustic technology (Echo550; nanoliter range), incubate for 20 minutes at room temperature
5. Deliver $^{33}$P-ATP (specific activity 10 μCi/μl) into the reaction mixture to initiate the reaction.
6. Incubate kinase reaction for 2 hours at room temperature
7. Reactions are spotted onto P81 ion exchange paper
8. Detect kinase activity by filter-binding method.

Activities of compounds are summarized below based on the range of IC50: +: >1 μM; ++: 0.1-1 μM; +++: 10-100 nM; ++++: <10 nM; NT: not tested. Examples 3, 4, 7, 9 are potent and selective Jak1 inhibitors.

| Example | Jak1 | Jak2 |
|---|---|---|
| 1 | ++ | NT |
| 2 | ++ | NT |
| 3 | ++++ | ++ |
| 4 | ++++ | ++ |
| 5 | + | + |
| 6 | + | + |
| 7 | ++++ | ++ |
| 8 | ++ | + |
| 9 | ++++ | ++ |
| 11 | ++++ | +++ |

Example B2: Human Whole Blood p-STAT3 Assay

Materials and Reagents:

1. Whole blood samples from human donors
2. IL-6 (R&D systems; Cat #206-IL)
3. Thrombopoietin (TPO; R&D systems; Cat #288-TP)
4. Red Blood Cell Lysis Buffer (Qiagen, Cat #79217)
5. ELISA kit for pSTAT3 (Invitrogen; Cat # KH00481)

Instruments:

1. Centrifuge
2. Envision; absorbance at 450 nm

Procedure:

1. 150 μl heparinized blood sample/tube.
2. Compounds at various concentrations is added to the blood, incubate for 10 min at RT (10 doses, 2 replicates for each compound).
3. Add IL-6 (final concentration: 100 ng/ml) or TPO (final conc: 50 ng/ml) to the blood for 15 min.
4. After the stimulation, add 0.6 mL RBC lysis buffer (Qiagen 79217) and mix and rock for 1-2 minutes at room temperature before centrifugation to remove lyzed RBCs. This step may be repeated once if RBCs are not lyzed completely. Harvest the WBCs.
5. Add 200 μl cell lysis buffer, ice 30 min.
6. Centrifuge at 16,000 g, 10 min, 4° C.
7. Transfer the supernatant to a new tube as cell lysate.
8. Run ELISA procedure according to the product instruction of ELIA kit.

In these assays, Examples 3, 4 and 7 showed selective inhibition of IL-6 induced STAT3 phosphorylation, but not TPO induced STAT3 phosphorylation as shown below based on the range of IC50: +: >100 μM; ++: 20-100 μM; +++: 5-20 μM; ++++: <5 μM. Example 11 also showed some activity in the TPO induced STAT3 phosphorylation assay.

| Example | IL-6 | TPO |
|---|---|---|
| 3 | ++++ | + |
| 4 | ++++ | + |
| 7 | ++++ | + |
| 11 | ++++ | ++ |

What is claimed:

1. A compound of formula I:

I

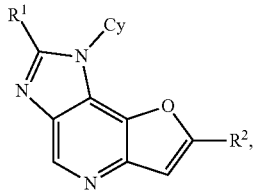

or a pharmaceutically acceptable salt thereof, wherein $R^1$ is H, halo, or $C_{1-3}$ alkyl optionally substituted with 1, 2, or 3 substituents independently selected from the group consisting of halo, OH, CN, OR, NHR, NRR', N(R)C(=O)R', [N(R)C(=O)(0)R',] *N(R)C(=O)(O)R',* OC(=O)NRR', C(=O)R, C(=O)NRR', $N(R)S(O)_2R'$, $S(O)_2R$, and $S(O)_2NRR'$;

$R^2$ is H, halo, or $C_{1-3}$ alkyl;

Cy is $C_{3-7}$ cycloalkyl, 3-7 membered heterocyclyl, phenyl, or 5-6 membered heteroaryl, each optionally substituted with 1, 2, or 3 substituents independently selected from the group consisting of $R^3$, oxo, halo, OH, CN, OR, NHR, NRR', N(R)C(=O)R', N(R)C(=O)(O)R', OC(=O)NRR', C(=O)R, C(=O)NRR', $N(R)S(O)_2R'$, $S(O)_2R$, and $S(O)_2NRR'$, wherein $R^3$ is $C_{1-3}$ alkyl optionally substituted with 1, 2, or 3 substituents independently selected from the group consisting of halo, OH, CN, OR, NHR, NRR', N(R)C(=O)R', N(R)C(=O)(O)R', OC(=O)NRR', C(=O)R, C(=O)NRR', $N(R)S(O)_2R'$, $S(O)_2R$, and $S(O)_2NRR'$; and R and R' are each independently H, or $C_{1-3}$ alkyl optionally substituted with 1, 2, or 3 substituents independently selected from the group consisting of halo, OH, and CN.

2. The compound of claim 1, wherein Cy is $C_{5-7}$ cycloalkyl, or 5-7 membered heterocyclyl, each optionally substituted with 1, 2, or 3 substituents independently selected from the group consisting of $R^3$, oxo, halo, OH, CN, OR, NHR, NRR', N(R)C(=O)R', N(R)C(=O)(O)R', OC(=O)NRR', C(=O)R, C(=O)NRR', $N(R)S(O)_2R'$, $S(O)_2R$, and $S(O)_2NRR'$, wherein $R^3$ is $C_{1-3}$ alkyl optionally substituted with 1, 2, or 3 substituents independently selected from the group consisting of halo, OH, CN, OR, NHR, NRR', N(R)C(=O)R', N(R)C(=O)(O)R', OC(=O)NRR', C(=O)R, C(=O)NRR', $N(R)S(O)_2R'$, $S(O)_2R$, and $S(O)_2RR'$.

3. The compound of claim 1, wherein $R^2$ is hydrogen.

4. The compound of claim 1, wherein the compound is selected from the group consisting of:

[trans-4-[2-[(R)-1-Hydroxyethyl]-1H-furo[3,2-b]imidazo[4,5-d]pyridin-1-yl] cyclohexanecarbonitrile (1), trans-4-[2-(Hydroxymethyl)furo[3,2-b]imidazo[4,5-d]pyridin-1-yl] cyclohexanecarbonitrile (2), 2-[trans-4-[2-[(R)-1-Hydroxyethyl]furo[3,2-b]imidazo[4,5-d]pyridin-1-yl]cyclohexyl] acetonitrile (3), 2-[(2R,5S)-5-[2-[(R)-1-Hydroxyethyl]furo[3,2-b]imidazo[4,5-d]pyridin-1-yl] tetrahydropyran-2-yl]acetonitrile (4), 3-[2-[(R)-1-Hydroxyethyl]-1H-furo[3,2-b]imidazo[4,5-d]pyridin-1-yl]-N-(2,2,2-trifluoroethyl)pyrrolidine-1-carboxamide (5), (R)-4-[2-(1-Hydroxyethyl)-1H-furo[3,2-b]imidazo[4,5-d]pyridin-1-yl]-N-(2,2,2-trifluoroethyl)piperidine-1-carboxamide (6), 2-[(2R,5S)-5-[2-(Hydroxymethyl)furo[3,2-b]imidazo[4,5-d]pyridin-1-yl]tetrahydropyran-2-yl]acetonitrile (7), 2-[(2S,5S)-5-[2-(Hydroxymethyl)furo[3,2-b]imidazo[4,5-d]pyridin-1-yl]tetrahydropyran-2-yl]acetonitrile (8), 2-[(2R,5S)-5-[2-Ethylfuro[3,2-b]imidazo[4,5-d]pyridin-1-yl] tetrahydropyran-2-yl]acetonitrile (9), 2-[(2R,5S)-5-[2-Furo[3,2-b]imidazo[4,5-d] pyridin-1-yl] tetrahydropyran-2-yl]acetonitrile (10), and 2-[(2R,5S)-5-[2-Methylfuro [3,2-b] imidazo [4,5-d] pyridin-1-yl] tetrahydropyran-2-yl] acetonitrile (11).]

*2-[(2R,5S)-5-[2-Ethylfuro[3,2-b]imidazo[4,5-d]pyridin-1-yl]tetrahydropyran-2-yl]acetonitrile (9),*

*2-[(2R,5S)-5-[2-Furo[3,2-b]imidazo[4,5-d]pyridin-1-yl] tetrahydropyran-2-yl]acetonitrile (10), and*

*2-[(2R,5S)-5-[2-Methylfuro[3,2-b]imidazo[4,5-d]pyridin-1-yl]tetrahydropyran-2-yl]acetonitrile (11).*

5. A method of treating rheumatoid arthritis in a subject comprising administering to the subject a compound of claim 1.

6. A compound of formula A1-14:

A1-14

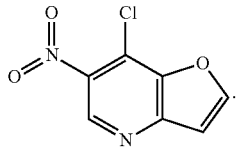

7. A process, comprising contacting a compound of formula V:

V

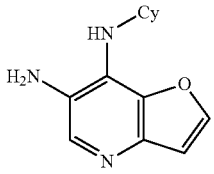

and a compound of formula VI:

VI

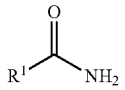

in the presence of a $(C_{1-6})_3$ alkyloxonium tetrafluoroborate at a sufficient temperature, and for a sufficient time to produce a compound of formula I:

I

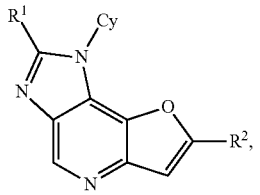

wherein $R^1$ is H, halo, or $C_{1-3}$ alkyl optionally substituted with 1, 2, or 3 substituents independently selected from the group consisting of halo, OH, CN, OR, NHR, NRR', N(R)C(=O)R', N(R)C(=O)(O)R', OC(=O)NRR', C(=O)R, C(=O)NRR', N(R)S(O)$_2$R', S(O)$_2$R, and S(O)$_2$NRR';

$R^2$ is H;

Cy is $C_{3-7}$ cycloalkyl, 3-7 membered heterocyclyl, phenyl, or 5-6 membered heteroaryl, each optionally substituted with 1, 2, or 3 substituents independently selected from the group consisting of $R^3$, oxo, halo, OH, CN, OR, NHR, NRR', N(R)C(=O)R', N(R)C(=O)(O)R', OC(=O)NRR', C(=O)R, C(=O)NRR', N(R)S(O)$_2$R', S(O)$_2$R, and S(O)$_2$NRR', wherein $R^3$ is $C_{1-3}$ alkyl optionally substituted with 1, 2, or 3 substituents independently selected from the group consisting of halo, OH, CN, OR, NHR, NRR', N(R)C(=O)R', N(R)C(=O)(O)R', OC(=O)NRR', C(=O)R, C(=O)NRR', N(R)S(O)$_2$R', S(O)$_2$R, and S(O)$_2$NRR'; and R and R' are each independently H, or $C_{1-3}$ alkyl optionally substituted with 1, 2, or 3 substituents independently selected from the group consisting of halo, OH, and CN.

8. The process of claim 7, wherein the $(C_{1-6})_3$ alkyloxonium tetrafluoroborate reagent is triethyloxonium tetrafluoroborate.

9. The process of claim 7, wherein the compound of formula V is prepared by a process comprising reducing a compound of formula VII:

VII

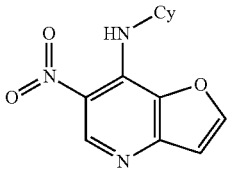

in the presence of a hydrogenation catalyst and hydrogen gas at a sufficient temperature, a sufficient pressure and for a sufficient time to produce a compound of formula V.

10. The process of claim 9, wherein the hydrogenation catalyst is palladium on carbon.

11. The process of claim 9, wherein the compound of formula VII is prepared by a process comprising contacting a compound of formula A1-14:

A1-14

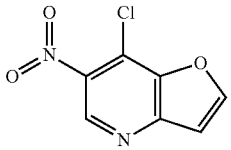

and a compound of formula VIII:

Cy-NH$_2$ VIII in the presence of a base at a sufficient temperature, and for a sufficient time to produce the compound of formula VII.

12. The process of claim 11, wherein the base is N,N-Diisopropylethylamine.

*13. The compound of claim 1, or a pharmaceutically acceptable salt thereof, wherein Cy is $C_{5-7}$ cycloalkyl, or 5-7 membered heterocyclyl, each optionally substitutued with 1, 2, or 3 substituents independently selected from the group consisting of $R^3$, oxo, halo, OH, CN, OR, NHR, NRR', N(R)C(=O)R', N(R)C(=O)(O)R', OC(=O)NRR', C(=O)R, C(=O)NRR', N(R)S(O)$_2$R', S(O)$_2$R, and S(O)$_2$NRR', wherein $R^3$ is $C_{1-3}$ alkyl optionally substituted with 1, 2, or 3 substituents independently selected from the group consisting of halo, OH, CN, OR, NHR, NRR', N(R)C(=O)R', N(R)C(=O)(O)R', OC(=O)NRR', C(=O)R, C(=O)NRR', N(R)S(O)$_2$R', S(O)$_2$R, and S(O)$_2$NRR'.*

*14. The compound of claim 1, or a pharmaceutically acceptable salt thereof, wherein $R^2$ is hydrogen.*

*15. The compound of claim 1, or a pharmaceutically acceptable salt thereof, wherein the compound or pharmaceutically acceptable salt is selected from the group consisting of:*

*2-[(2R,5S)-5-[2-Ethylfuro[3,2-b]imidazo[4,5-d]pyridin-1-yl]tetrahydropyran-2-yl]acetonitrile (9),*

*2-[(2R,5S)-5-[2-Furo[3,2-b]imidazo[4,5-d]pyridin-1-yl]tetrahydropyran-2-yl]acetonitrile (10),*

*2-[(2R,5S)-5-[2-Methylfuro[3,2-b]imidazo[4,5-d]pyridin-1-yl]tetrahydropyran-2-yl]acetonitrile (11), and pharmaceutically acceptable salts thereof.*

*16. A compound that is 2-[(2R,5S)-5-[2-Methylfuro[3,2-b]imidazo[4,5-d]pyridin-1-yl]tetrahydropyran-2-yl]acetonitrile (11).*

*17. A pharmaceutically acceptable salt that is a pharmaceutically acceptable salt of 2-[(2R,5S)-5-[2-Methylfuro[3,2-b]imidazo[4,5-d]pyridin-1-yl]tetrahydropyran-2-yl]acetonitrile (11).*

*18. A method of treating rheumatoid arthritis in a subject in need thereof comprising administering to the subject in need thereof an effective amount of a compound of claim 1, or a pharmaceutically acceptable salt thereof.*

*19. A compound of formula A1-14:*

A1-14

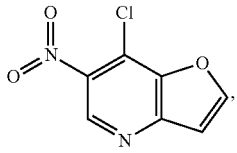

*or a pharmaceutically acceptable salt thereof.*

*20. A process, comprising contacting a compound of formula V:*

V

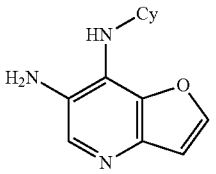

*and a compound of formula VI:*

VI

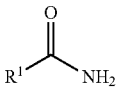

*in the presence of a ($C_{1-6}$ alkyl)$_3$oxonium tetrafluoroborate at a sufficient temperature, and for a sufficient time to produce a compound of formula I:*

I

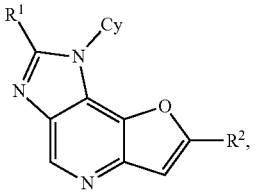

*or a pharmaceutically acceptable salt thereof, wherein $R^1$ is H, halo, or $C_{1-3}$ alkyl optionally substituted with 1, 2, or 3 substituents independently selected from the group consisting of halo, OH, CN, OR, NHR, NRR', N(R)C(═O)R', N(R)C(═O)(O)R', OC(═O)NRR', C(═O)R, C(═O)NRR', N(R)S(O)$_2$R', S(O)$_2$R, and S(O)$_2$NRR'; $R^2$ is H;*

*Cy is $C_{3-7}$ cycloalkyl, 3-7 membered heterocyclyl, phenyl, or 5-6 membered heteroaryl, each optionally substituted with 1, 2, or 3 substituents independently selected from the group consisting of $R^3$, oxo, halo, OH, CN, OR, NHR, NRR', N(R)C(═O)R', N(R)C(═O)(O)R', OC(═O)NRR', C(═O)R, C(═O)NRR', N(R)S(O)$_2$R', S(O)$_2$R, and S(O)$_2$NRR', wherein $R^3$ is $C_{1-3}$ alkyl optionally substituted with 1, 2, or 3 substituents independently selected from the group consisting of halo, OH, CN, OR, NHR, NRR', N(R)C(═O)R', N(R)C(═O)(O)R', OC(═O)NRR', C(═O)R, C(═O)NRR', N(R)S(O)$_2$R', S(O)$_2$R, and S(O)$_2$NRR'; and*

*R and R' are each independently H, or $C_{1-3}$ alkyl optionally substituted with 1, 2, or 3 substituents independently selected from the group consisting of halo, OH, and CN.*

*21. The process of claim 20, wherein Cy is $C_{5-7}$ cycloalkyl or 5-7 membered heterocyclyl, each of which is optionally substituted with 1, 2, or 3 substituents independently selected from the group consisting of $R^3$, oxo, halo, OH, CN, OR, NHR, NRR', N(R)C(═O)R', N(R)C(═O)(O)R', OC(═O)NRR', C(═O)R, C(═O)NRR', N(R)S(O)$_2$R', S(O)$_2$R, and S(O)$_2$NRR', wherein $R^3$ is $C_{1-3}$ alkyl optionally substituted with 1, 2, or 3 substituents independently selected from the group consisting of halo, OH, CN, OR, NHR, NRR', N(R)C(═O)R', N(R)C(═O)(O)R', OC(═O)NRR', C(═O)R, C(═O)NRR', N(R)S(O)$_2$R', S(O)$_2$R, and S(O)$_2$NRR'.*

*22. The process of claim 20, wherein the compound of formula I, or a pharmaceutically acceptable salt thereof, is selected from the group consisting of:*

*2-[(2R,5S)-5-[2-Ethylfuro[3,2-b]imidazo[4,5-d]pyridin-1-yl]tetrahydropyran-2-yl]acetonitrile (9),*

*2-[(2R,5S)-5-[2-Furo[3,2-b]imidazo[4,5-d]pyridin-1-yl]tetrahydropyran-2-yl]acetonitrile (10),*

*2-[(2R,5S)-5-[2-Methylfuro[3,2-b]imidazo[4,5-d]pyridin-1-yl]tetrahydropyran-2-yl]acetonitrile (11), and pharmaceutically acceptable salts thereof.*

* * * * *